US010213295B2

(12) United States Patent
Kobayashi et al.

(10) Patent No.: US 10,213,295 B2
(45) Date of Patent: Feb. 26, 2019

(54) INTRAOCULAR LENS INSERTION APPARATUS

(71) Applicant: KOWA COMPANY, LTD., Nagoya-shi, Aichi (JP)

(72) Inventors: Kenichi Kobayashi, Nagoyi (JP); Genyo Midorikawa, Nagoya (JP)

(73) Assignee: Kowa Company, Ltd., Nagoya-shi, Aichi (JP)

(*) Notice: Subject to any disclaimer, the term of this patent is extended or adjusted under 35 U.S.C. 154(b) by 8 days.

(21) Appl. No.: 14/907,184

(22) PCT Filed: Jul. 24, 2014

(86) PCT No.: PCT/JP2014/069573
§ 371 (c)(1),
(2) Date: Jan. 22, 2016

(87) PCT Pub. No.: WO2015/012355
PCT Pub. Date: Jan. 29, 2015

(65) Prior Publication Data
US 2016/0175090 A1 Jun. 23, 2016

(30) Foreign Application Priority Data

Jul. 24, 2013 (JP) ................................ 2013-153752

(51) Int. Cl.
*A61F 2/16* (2006.01)
(52) U.S. Cl.
CPC ............ *A61F 2/167* (2013.01); *A61F 2/1662* (2013.01); *A61F 2/1678* (2013.01)

(58) Field of Classification Search
CPC ....... A61F 2/1662; A61F 2/167; A61F 2/1678
See application file for complete search history.

(56) References Cited

U.S. PATENT DOCUMENTS

2002/0173756 A1* 11/2002 Waldock ................. A61F 9/013
604/294
2008/0312661 A1* 12/2008 Downer ................ A61F 2/1678
606/107

(Continued)

FOREIGN PATENT DOCUMENTS

EP          2641568 A1    9/2013
JP        2008-307376 A   12/2008

(Continued)

OTHER PUBLICATIONS

Extended European Search Report issued in corresponding European Patent Application No. 14828661.0, dated Feb. 9, 2017.

(Continued)

*Primary Examiner* — Katherine Rodjom
(74) *Attorney, Agent, or Firm* — Knobbe, Martens, Olson & Bear, LLP

(57) ABSTRACT

Intraocular lens insertion apparatus includes a cylindrical body member configured to retain an intraocular lens, a fore-end opening provided for a tip of the body member, and a planate protrusion provided for a tip of the fore-end opening. Further, an end surface of the fore-end opening is an oblique surface which is oblique to a plane perpendicular to a central axis of the body member, and a fore-end area including a pair of lateral walls which are parallel to each other across the central axis is formed on a side of the tip of the fore-end opening.

8 Claims, 25 Drawing Sheets

(56) References Cited

U.S. PATENT DOCUMENTS

2009/0292294 A1* 11/2009 Tanaka .................. A61F 2/1678
606/107
2013/0331853 A1 12/2013 Marunaka et al.

FOREIGN PATENT DOCUMENTS

| JP | 2009-160153 A | 7/2009 |
|---|---|---|
| JP | 2012-125361 A | 7/2012 |
| WO | WO 2012/I081419 A1 | 6/2012 |

OTHER PUBLICATIONS

International Search Report for International Application No. PCT/JP2014/069573, dated Oct. 28, 2014.
Notification of Reasons for Refusal issued in corresponding Japanese Patent Application No. 2015-528334 dated Apr. 24, 2018.
Notification of Reasons for Refusal received in connection with Japanese Patent Application No. 2015-528334 dated Oct. 5, 2018.
Notification of Reasons for Refusal received in connection with Japanese Patent Application No. 2015-528334 dated Oct. 16, 2018.

* cited by examiner

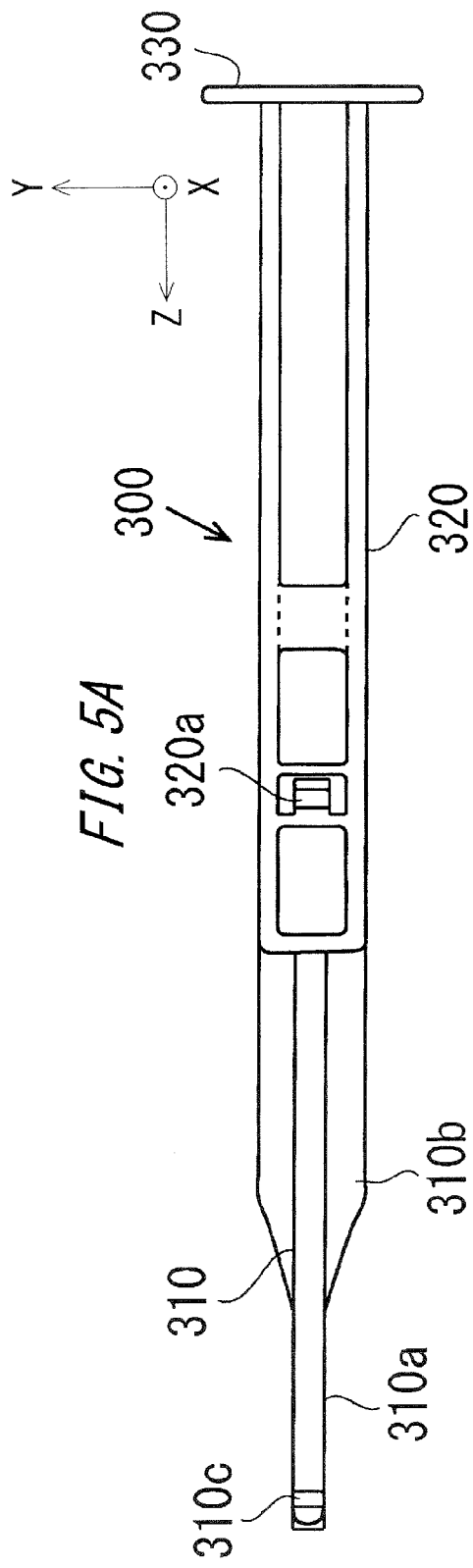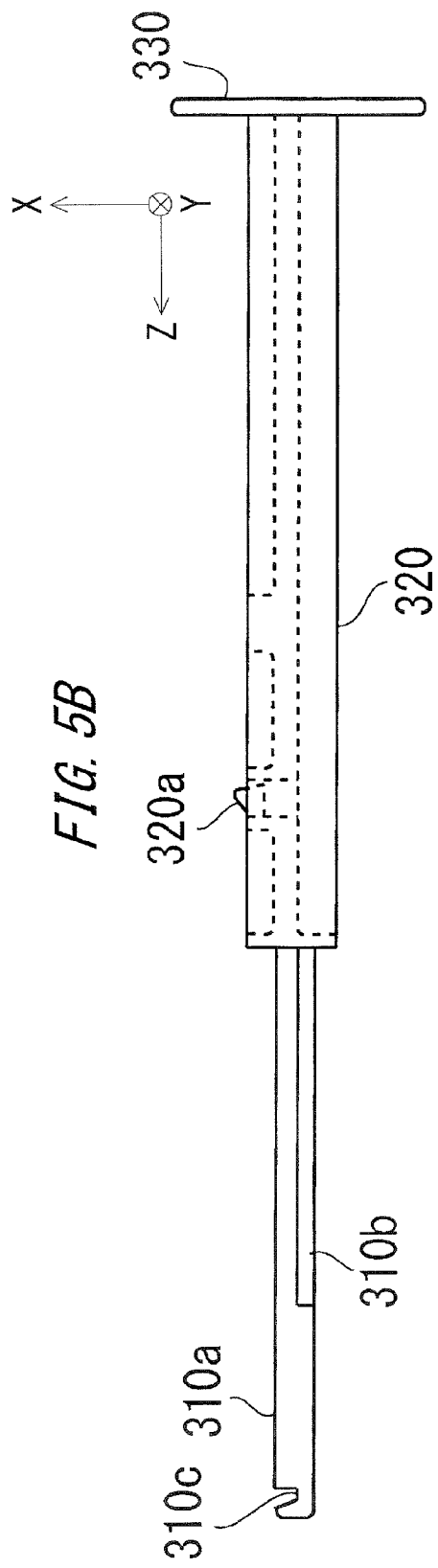

1100

1100

1100

1100

1100

1100

1100

1100

FIG. 11H
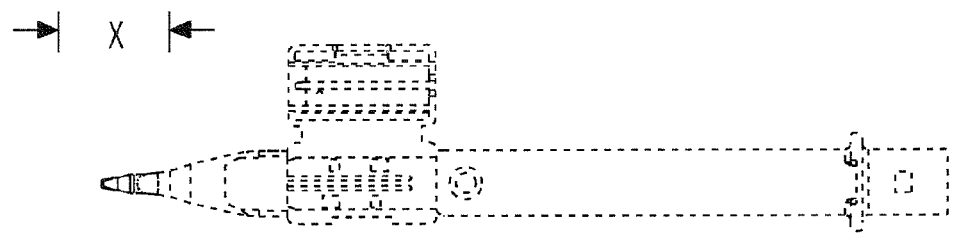
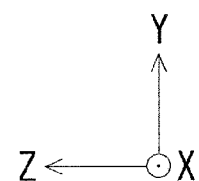
1100
FIG. 11I
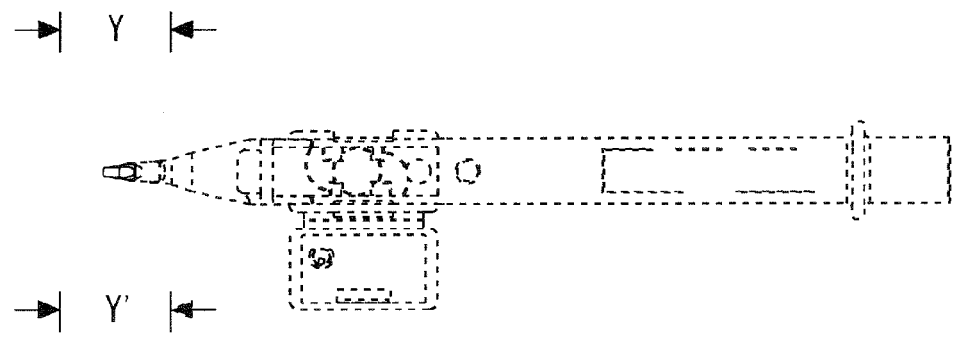
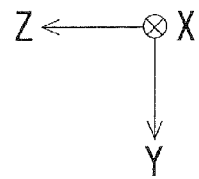
1100

1100

1100

INTRAOCULAR LENS INSERTION APPARATUS

CROSS-REFERENCE TO RELATED APPLICATION

This application is based upon and claims the benefit of priority of the prior Japanese Patent Application No. 2013-153752, filed on Jul. 24, 2013, the entire contents of which are incorporated herein by reference.

FIELD

The embodiments discussed herein pertain to an intraocular lens insertion apparatus.

BACKGROUND

Intraocular lenses are widely used to be replaced with human opacity crystalline lenses in cataract treatments or normal human crystalline lenses for compensating the optical powers of the lenses. In intraocular lens insertion surgeries for the cataract treatments, a discission wound which is several millimeters in length is produced at the edge of the cornea, the human crystalline lens is crushed and removed by phacoemulsification and aspiration etc. and the intraocular lens is inserted and fixed in the eye, for example.

Polymethyl methacrylate (PMMA), acrylic resin, silicon resin etc. are used as the material of the intraocular lens. The structure of the intraocular lens can be divided into an optical member and a supporting member. The intraocular lens is enclosed in a dedicated intraocular lens insertion apparatus. When the intraocular lens is used, the intraocular lens insertion apparatus is taken out from the package of the apparatus in an aseptic manner, and the tip of the insertion apparatus is inserted into the eye from the discission wound and the insertion apparatus is handled to guide the intraocular lens into the human crystalline lens capsule.

It is desirable that the discission wound be as small as possible in order to mitigate the burden of the patient. Therefore, the insertion apparatus is configured to eject the intraocular lens into the eye in a folded state.

For example, patent document 1 discloses a structure in which the opening of the tip of the insertion apparatus is configured to have an oblique surface oblique to the longitudinal direction of the opening. In addition, a roof is provided for the tip of the opening. The roof functions to open the wound when the tip of the insertion apparatus is inserted into the wound. Further, patent document 2 discloses a structure in which the end surface of the opening of the tip of the insertion apparatus is formed in a curved shape. Therefore, the possibility that the insertion apparatus unnecessarily stimulates the eye tissues can be reduced since the opening in the curved shape can make a smooth contact with the wound etc. when the tip of the insertion apparatus is inserted into the wound.

CITATION LIST

Patent Literature

[PTL 1] Japanese Patent Application Laid-Open Publication No. 2008-307376
[PTL 2] Japanese Patent Application Laid-Open Publication No. 2009-160153

SUMMARY

Technical Problem

However, when the discission wound becomes smaller, the insertion apparatus with the opening having the shape as described in the above patent documents may face a difficulty in insert the opening into a predetermined position in the discission wound. In addition, when the opening is not completely inserted into the discission wound and the insertion apparatus is handled to eject the intraocular lens into the human crystalline lens capsule, the intraocular lens may go out from a part of the opening which is located outside of the discission wound and then the intraocular lens cannot be inserted into the eye.

One aspect of the present invention lies in providing an insertion apparatus which prevents an intraocular lens from going out to the outside of the eye and ensures a secure insertion of the intraocular lens into the eye when the insertion apparatus is inserted a discission wound which is smaller than that of conventional discission wounds.

Solution to Problem

According to an embodiment, it is provided an intraocular lens insertion apparatus, including a cylindrical body member configured to retain an intraocular lens, a fore-end opening provided for a tip of the body member, and a planate protrusion provided for a tip of the fore-end opening, wherein an end surface of the fore-end opening is an oblique surface which is oblique to a plane perpendicular to a central axis of the body member, and a fore-end area including a pair of lateral walls which are parallel to each other across the central axis is formed on a side of the tip of the fore-end opening. Therefore, the insertion apparatus can be inserted into a discission wound smaller than conventional discission wounds, can prevent the intraocular lens from going out of the eye from the insertion apparatus and can stably retain and guide the intraocular lens into the human crystalline capsule.

In addition, the intraocular lens insertion apparatus can be configured to achieve that a back-end area which is connected with a back end of the fore-end area is formed on a side of a back end of the fore-end opening, and an angle of gradient of an oblique surface in the fore-end area to a plane perpendicular to the central axis is smaller than an angle of gradient of an oblique surface in the back-end area to a plane perpendicular to the central axis. Further, the contour of the fore-end opening in a side view can include an inflection point between the fore-end area and the back-end area. With such configurations, the lateral walls in the fore-end area in the side view are configured to rise at a steep angle and therefore the intraocular lens can be more stably retained by the lateral walls than the conventional insertion apparatus. Therefore, the intraocular lens can be prevented from going out of the eye from the fore-end opening when the intraocular lens is guided into the human crystalline capsule.

Further, the intraocular lens insertion apparatus can be configured to achieve that the shape of the fore-end opening is tapering toward the tip of the fore-end opening. Therefore, the tip of the fore-end opening can be more easily inserted into the eye than conventional insertion apparatuses after the insertion apparatus is inserted into the small discission wound. In addition, the body member can include a positioning member for positioning the intraocular lens, and the intraocular lens can be positioned by the positioning member in the body member in advance.

Advantageous Effects of Invention

According to an embodiment, an insertion apparatus which prevents an intraocular lens from going out to the outside of the eye and ensures a secure insertion of the intraocular lens into the eye when the insertion apparatus is inserted a discission wound which is smaller than that of a conventional discission wound can be achieved.

BRIEF DESCRIPTION OF DRAWINGS

FIGS. 5A and 5B are diagrams schematically illustrating a plunger for an intraocular lens according to an embodiment;

FIG. 11H is a diagram illustrating a nozzle body of an intraocular lens insertion apparatus according to a variation example;

FIG. 11I is a diagram illustrating a nozzle body of an intraocular lens insertion apparatus according to a variation example;

DESCRIPTION OF EMBODIMENTS

First, an intraocular lens insertion apparatus according to one embodiment is described below with reference to the drawings. However, it is to be understood that the following descriptions are exemplary and explanatory for the intraocular lens insertion apparatus, and are not restrictive of the invention, as claimed.

Figure 1A:
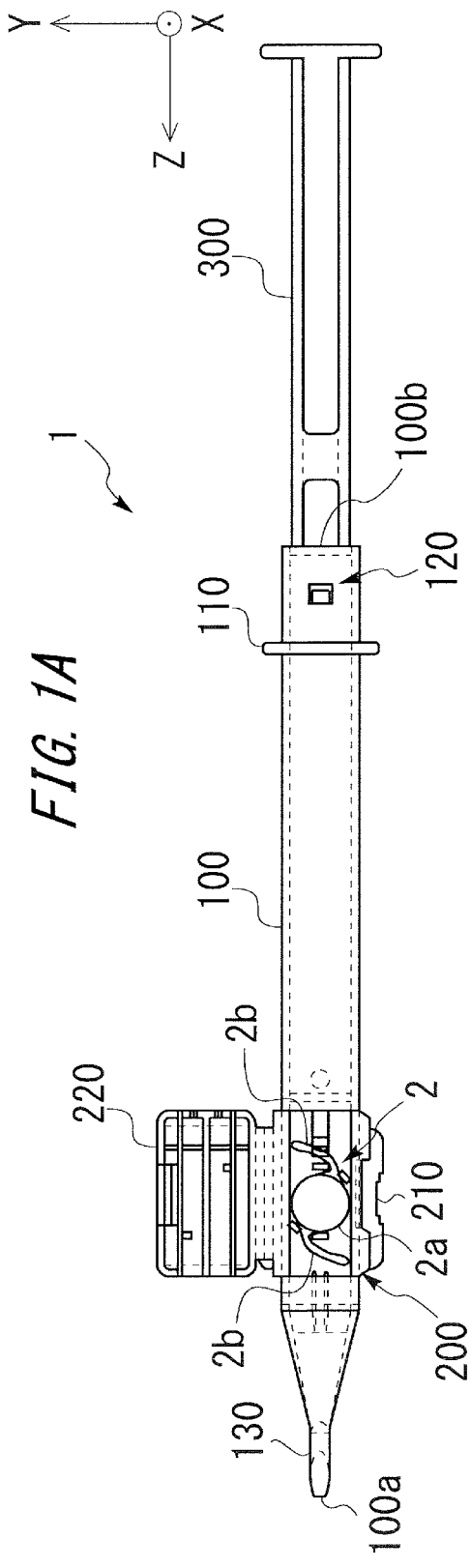
FIGS. 1A and 1B are diagrams schematically illustrating an intraocular lens insertion apparatus according to an embodiment.
Figure 1B:
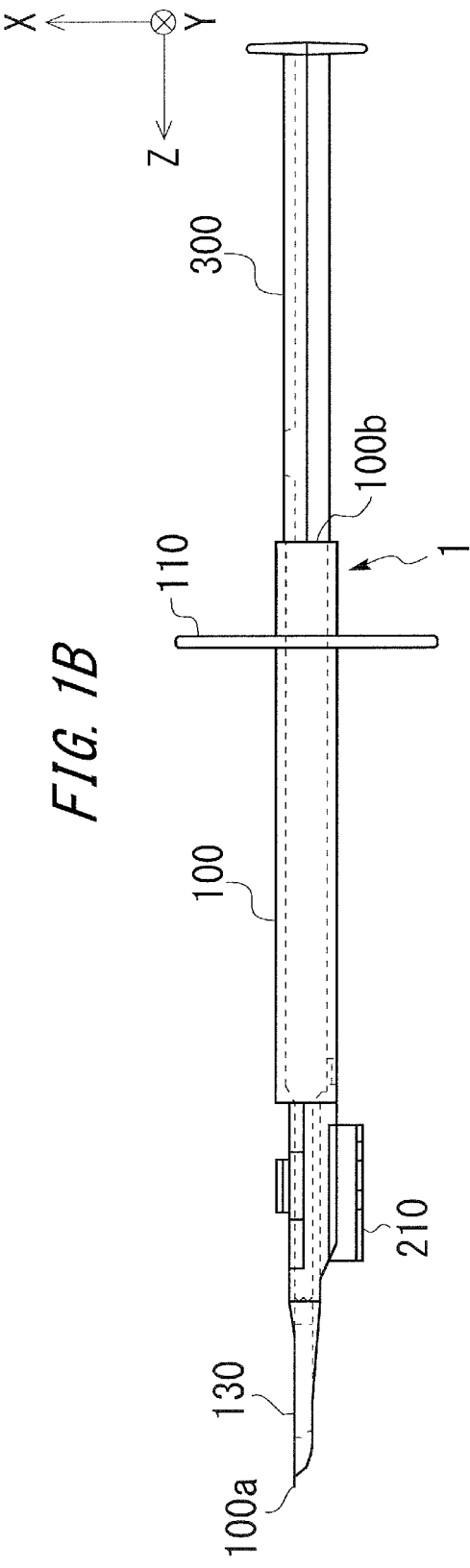

As illustrated in FIGS. 1A and 1B, the intraocular lens insertion apparatus 1 according to the first embodiment includes a nozzle body 100, a stage member 200 and a plunger 300. The nozzle body 100 is formed into a shape similar to an elongated tube and a hollow space is provided over the entire length of the nozzle body 100. It is noted that the nozzle body 100 corresponds to an example of the body of the intraocular lens insertion apparatus. The cross-section of the nozzle body 100 formed by a surface which is vertical to the longitudinal direction of the nozzle body 100 is approximately rectangular. Further, an intraocular lens 2 is retained in the nozzle body 100 by the stage member. The plunger 300 is a bar member which is elongated tube in shape. The plunger 300 is partially inserted into the tube portion of the nozzle body 100. The plunger 300 is used as a push member used for guiding the intraocular lens 2 into the human crystalline lens capsule.

As illustrated in FIGS. 1A and 1B, the Z axis is set so that the direction of the Z axis is parallel to the longitude direction of the insertion apparatus 1 and the direction of the Z axis going from the back end to the front end of the nozzle body 100 is the positive direction. And the X axis and the Y axis are set to bisect each other at right angles and to be perpendicular to the Z axis. As described below, the X axis corresponds to the optic axis of the intraocular lens 2 which is set by the positioning member 210 in the nozzle body 100. In addition, the Z axis is parallel to the direction in which the plunger 300 inserted into the nozzle body 100 is pushed. It is noted in the following descriptions of each member that a surface provided in the negative side of the X axis is referred to as a bottom surface and that a surface provided in the positive side of the X axis is referred to an upper surface in some cases. Moreover, it is also noted that the positive side of the X axis, the negative side of the X axis, the positive side of the Z axis and the negative side of the Z axis are referred to as an upward direction, a downward direction, a forward direction and a backward direction, respectively in some cases.

A holding member 110 which is planate in shape is provided near the back end 100b of the nozzle body 100 to protrude from the nozzle body 100 in the X axis direction and Y axis direction. The user of the insertion apparatus places a finger on the holding member 110 when the user pushes the plunger 300 toward the tip 100a of the nozzle body 100. In addition, a latching hole 120 is provided for the nozzle body 100 on the side of the back end 100b to the holding member 110. The latching hole 120 is used as retaining member for retaining the plunger 300 in the nozzle body 100. When a protruding member which protrudes from the plunger 300 in the positive direction of the X axis engage with the latching hole 120 with the plunger 300 inserted into the nozzle body 100, the relative position of the plunger 300 to the nozzle body 100 is fixed. When the user pushes the plunger 300 toward the tip 100a of the nozzle body 100, the protruding member of the plunger 300 moves toward the tip 100a of the nozzle body 100 to be released from the engagement with the latching hole 120.

Further, a stage member 200 is provided near the tip 100a of the nozzle body 100. The stage member 200 includes a positioning member 210 and a stage lid member 220. The positioning member 210 is a member for settling the intraocular lens 2 on the stage member 200 while the insertion apparatus 1 is being transported and before the insertion apparatus is used. When the insertion apparatus 1 is manufactured, the stage lid member 220 is opened and the intraocular lens 2 is set on the stage member 200 with the positioning member 210 attached to the stage member 200. And then, the user detaches the positioning member 210 from the stage member 200 with the stage lid member 220 closed. And, the user move the plunger 300 toward the tip 100a of the nozzle body 100 to thrust the intraocular lens 2 from the insertion tube 130 while the intraocular lens 2 is pushed by the plunger 300. It is noted that the nozzle body 100, the stage member 200 and the plunger 300 is formed from resin such as polypropylene. Polypropylene has been proven as a material used for medical apparatuses. In addition, polypropylene demonstrates an advantageous biocompatibility and is reliable in chemical resistance etc.

Figure 2A:
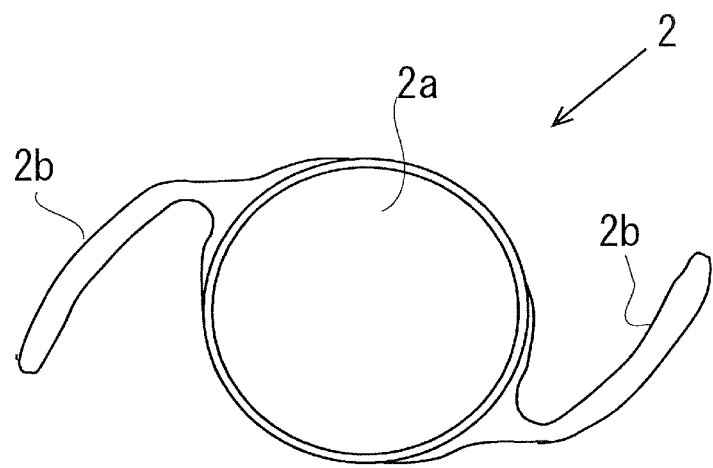
FIGS. 2A and 2B are diagrams schematically illustrating an intraocular lens according to an embodiment.
Figure 2B:
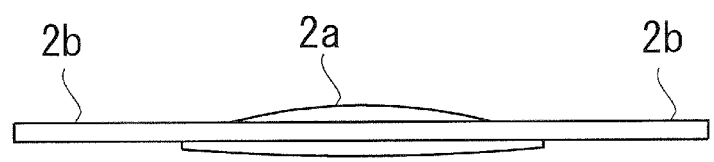

FIGS. 2A and 2B are diagrams schematically illustrating the configuration of the intraocular lens 2. FIG. 2A is a plan diagram of the intraocular lens 2, and FIG. 2B is a side diagram of the intraocular lens 2. The intraocular lens 2 includes an optical member 2a with a predetermined power and supporting members 2b provided for the optical member 2a. The supporting member 2b is a member for settling the optical member 2a in the eye. The optical member 2a and the supporting members 2b are formed from a flexible resin material.

Figure 3:
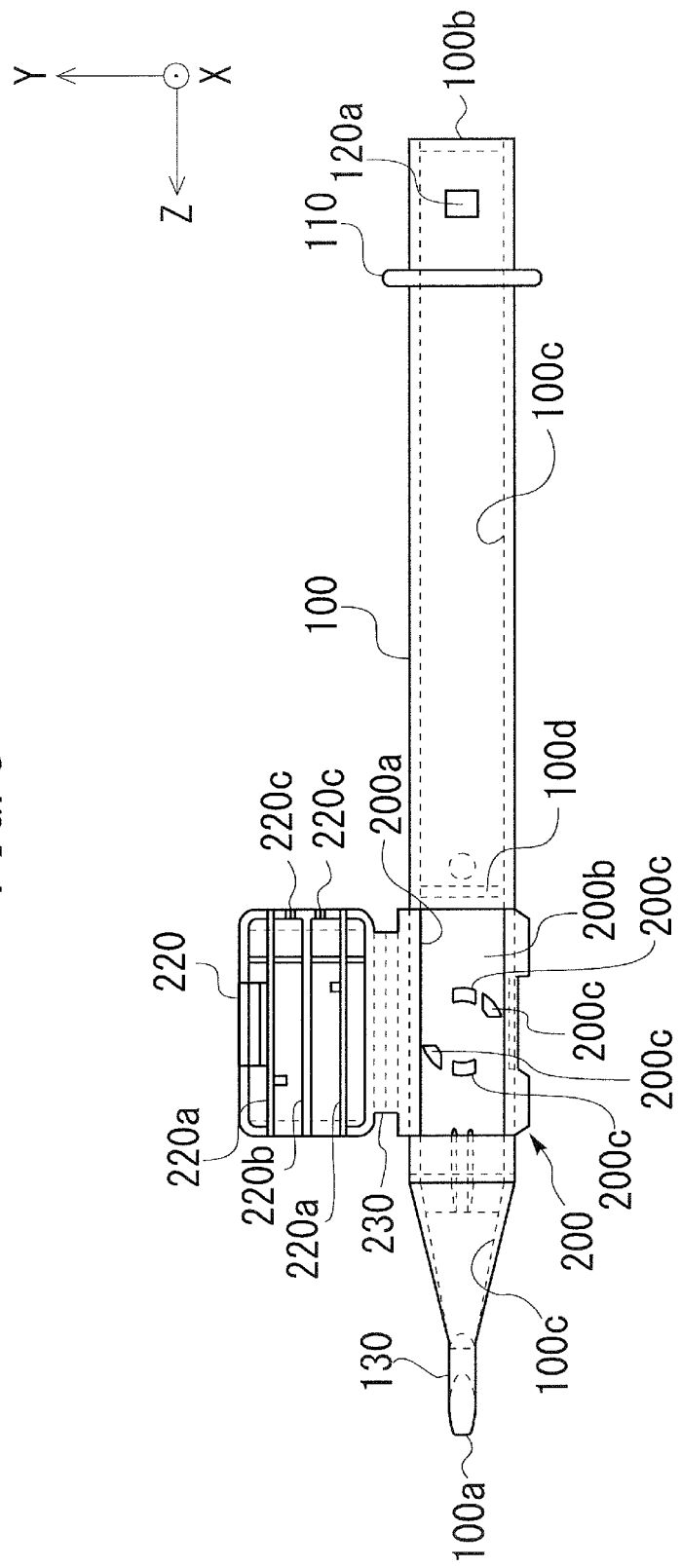
FIG. 3 is a diagram schematically illustrating a nozzle body of an intraocular lens insertion apparatus according to an embodiment.

FIG. 3 is a plane diagram of the nozzle body 100. The intraocular lens 2 is set on the stage member 200 of the nozzle body 100. And the intraocular lens 2 is pushed by the plunger 300 and thrust from the insertion tube 130. It is noted that a through-hole 100c is provided for the nozzle body 100. The cross-section shape of the through-hole 100c varies according to the change of the contour of the nozzle body 100. When the intraocular lens 2 is thrust from the insertion tube 130, the intraocular lens 2 is deformed according to the change of the cross-section shape of the through-hole 100c of the nozzle body 100 into a shape in which the intraocular lens 2 can be easily inserted into the discission wound of the patient's eye.

A stage groove 200a is formed on the stage member 200. The width of the stage groove 200a is slightly larger than the outside diameter of the optical member 2a of the intraocular lens 2. The dimension of the stage groove 200a in the Z axis direction is configured to be larger than the whole length of the intraocular lens 2 including the supporting members 2b which extend from the both sides of the intraocular lens 2. In addition, the bottom surface of the stage groove 200a forms a setting surface 200b. The position of the setting surface 200b in the X axis direction is set to be on the positive side of the X axis to the position of the bottom surface of the through-hole 100c of the nozzle body 100. It is assumed here that the bottom surface of the through-hole 100c is a surface which is parallel to the Y-Z plane and is provided on the negative side of the X axis in the internal surface of the through-hole 100c in FIG. 3. It is noted in the following descriptions of other members that the bottom surfaces have similar meanings. The setting surface 200b and the bottom surface of the through-hole 100c are connected with each other by the bottom slant surface 100d.

The stage member 200 and the stage lid member 220 are formed as a unit. The dimension of the stage lid member 220 in the Z axis direction is similar to the dimension of the stage member 200. The stage lid member 220 is connected with the stage member 200 by a laminated connection member 230 which is formed by extending the side surface of the stage member 200 toward stage lid member 220. The connection member 230 is configured to fold in half and the stage lid member 220 can overlap the stage member 200 from the positive side of the X axis by folding the connection member 230.

Ribs 220a and 220b are provided on the surface which the setting surface 200b faces when the stage lid member 220 is closed for reinforcing the stage lid member 220 and settling the intraocular lens 2 in the stage member 200. In addition, a guide protrusion 220c is provided as a guide of the plunger 300 when the plunger 300 is pushed toward the tip 100a of the nozzle body 100.

Figure 4A:
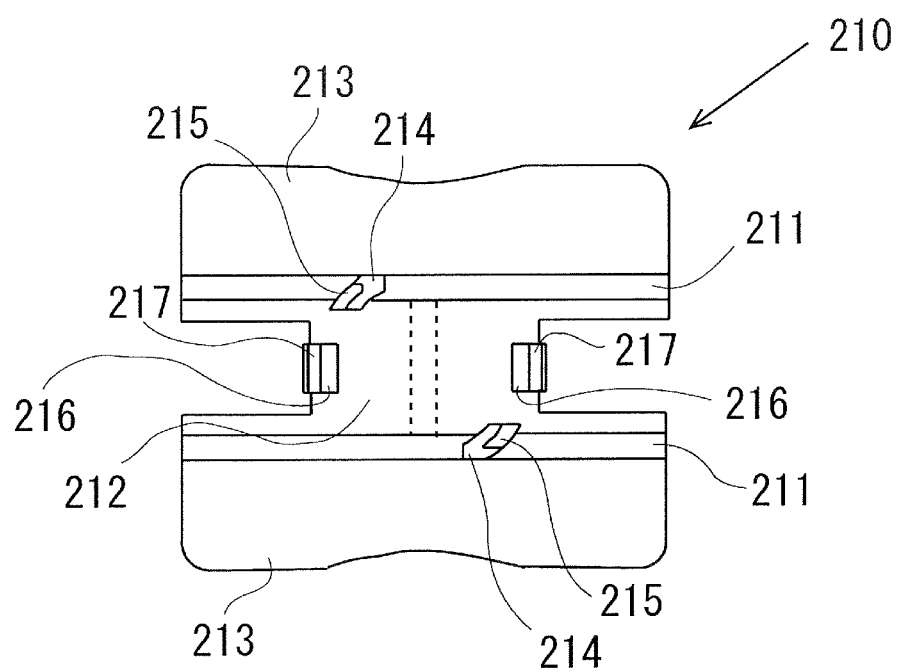
FIG. 4 is a diagram schematically illustrating a positioning member of an intraocular lens insertion apparatus according to an embodiment.
Figure 4B:
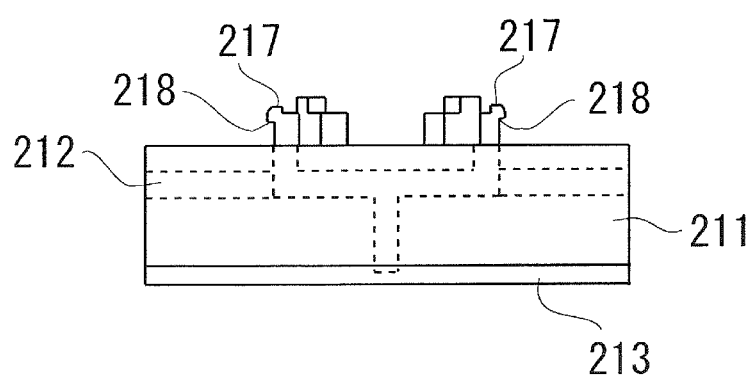

The positioning member 210 is detachably provided beneath the setting surface 220b of the stage member 200, that is on the negative side of the X axis. FIGS. 4A and 4B schematically illustrate the configurations of the positioning member 210. FIG. 4A is a plane diagram illustrating the positioning member 210, and FIG. 4B is a side diagram thereof. The positioning member 210 is configured as a member separated from the nozzle body 100. Side wall members 211 are connected with each other by a connection member 212 to form a pair. A retaining member 213 extending outward is provided at the lower end of each side wall member 211.

A pair of first settling members 214 protruding upward is formed on the upper end of each side wall member 211. The shape of the first settling member 214 when the member is viewed from above is arc. In addition, a first positioning member 215 protruding upward is formed on the side of the outer circumference of the upper end surface of the first settling member 214. The distance between internal circles of the first positioning members 215 is slightly larger than the diameter of the optical member 2a of the intraocular lens 2.

In addition, a pair of the second settling members 216 protruding upward is formed on both ends in the front-back direction of the connecting member 212. The shape of the first settling member 216 when the member is viewed from above is rectangular. The height of the second settling member 216 is similar to the height of the upper end surface of the first settling member 214. Further, a second positioning member 217 protruding upward as a whole is formed on the side of the outer circumference of the second settling member 216 from the right end to the left end of the second settling member 216. The distance between the second positioning members 217 is slightly larger than the diameter of the optical member 2a of the intraocular lens 2. Moreover, as illustrated in FIG. 4B, a latching protrusion 218 slightly protruding in the forward and backward direction is formed on the upper end of the second settling member 216 from the right end to the left end of the second settling member 216.

In the present embodiment, the positioning member 210 is assembled from the underside of the setting surface 200b of the nozzle body 100, that is from the negative side of the X axis. Four setting surface through-holes are formed on the setting surface 200b of the nozzle body 100 to penetrating the nozzle body 100 through in the thickness direction of the nozzle body 100. The shape of the setting surface through-hole 200c is similar to and slightly larger than the shape of the first settling member 214 and the shape of the second settling member 216 of the positioning member 210 when the first settling member 214 and the second settling member 216 are viewed from above, that is, from the positive side of the X axis. Further, when the positioning member 210 is attached to the nozzle body 100, the first settling member 214 and the second settling member 216 are inserted into the setting surface through-holes 200c from beneath the setting surface 200b to protrude upward from the setting surface 200b.

Moreover, the latching protrusion 218 provided for the second settling member 216 is protruding from the setting surface 200b through the setting surface through-hole 200c and is fixed at the position above the setting surface 200b. Therefore, the positioning member 210 is assembled from beneath the nozzle body 100, and the first settling member 214 and the second settling member 216 are fixed with protruding from the setting surface 200b. When the intraocular lens 2 is set on the setting surface 200b, the bottom surface of the optical member 2a in the peripheral area of the optical member 2a is set on the upper surface of the first settling member 214 and the second settling member 216. In addition, the position of the optical member 2a in the Z axis direction is determined by the first positioning member 215 and the second positioning member 217.

FIG. 5 schematically illustrates the configuration of the plunger 300. The length of the plunger in the Z axis direction is slightly larger than the length of the nozzle body 100. The plunger 300 includes an action member 310 on the fore-end side of the plunger 300, that is on the positive side of the Z axis the shape of which is cylinder and an insertion member 320 on the back-end side of the plunger 300, that is on the negative side of the Z axis the shape of which is similar to a rectangular rod. The action member 310 includes a cylindrical member 310a and a flattened member 310b which forms a sheet expanding in the Y axis direction from the cylindrical member 310a.

A notch member 310c is formed at the tip of the action member 310. As illustrated in FIGS. 5A and 5B, the notch member 310c is configured to be a groove which opens toward the positive side of the X axis and penetrates the action member 310 through in the Y axis direction. Further, as illustrated in FIG. 5B, the end surface of the notch member 310c provided on the side of the tip of the action member 310 is configured to be an oblique surface which is ascending toward the positive side of the X axis as the position on the oblique surface becomes close to the tip of the action member 310.

On the other hand, the cross section of the insertion member 320 as a whole is H-shaped and the dimension of the insertion member 320 in the X axis direction and the Y axis direction is slightly smaller than the dimension of the through-hole 100c of the nozzle body 100. In addition, the pressing plate member 330 expanding in the x-y plane the shape of which is disk is provided at the back-end of the insertion member 320.

A notch 320a protruding toward the positive side of the X axis is formed at a part on the forward side to the center of the insertion member 320 in the Z axis direction. The notch 320a can be moved toward the X axis direction due to the flexibility of the material used for the plunger 300. When the plunger 300 is inserted into the nozzle body 100, the notch 320a is engaged with the latching hole 120a which is formed on the upper surface of the nozzle body and penetrates in the thickness direction of the nozzle body 100. And then, the relative position of the nozzle body 100 and the plunger 300 in their default positions is determined. It is noted that the positions where the notch 320a and the latching hole 120a are provided are determined to achieve that the tip of the action member 310 is positioned posterior to the optical member 2a of the intraocular lens 2 set on the stage member 200 and that the segment member 310c support the supporting member 2b of the optical member 2a from beneath.

The plunger 300 is inserted into the nozzle body 100 and set in the initial position before the insertion apparatus 1 as described above is used. In addition, the positioning member 210 is attached to the stage member 200 from beneath setting surface 200b as described above. Therefore, the first settling member 214 and the second settling member 216 of the positioning member 210 are fixed to protruding from the setting surface 200b.

Further, the intraocular lens 2 is settled on the first settling member 214 and the second settling member 216 in the state in which the supporting member 2b is positioned in the Z axis direction. In this state, since the peripheral part of the optical member is in contact with the first settling member 214 and the second settling member 216, the central part of the intraocular lens 2 is supported in an unloaded state. In addition, in this state, the supporting member 2b of the intraocular lens 2 is supported by the bottom surface of the segment member 310c of the plunger 300.

Moreover, the second settling member 216 functions as a stopper for preventing the plunger 300 from moving toward the tip 100a of the nozzle body 100. Therefore, the plunger 300 cannot move unless the positioning member 210 is detached from the nozzle body 100.

When the intraocular lens 2 is guided into the eye of the patient by the insertion apparatus 1, the positioning member 210 is detached from the nozzle body 100 first. As a result, the first settling member 214 and the second settling member 216 supporting the optical member 2a of the intraocular lens 2 is receded from the setting surface 200b and then the intraocular lens 2 is settled on the setting surface 200b. Since the setting surface 200b is flat, the intraocular lens 2 can be securely settled on the setting surface 200b. In addition, since the width of the stage groove 200a is configured to be slightly larger than the diameter of the optical member 2a of the intraocular lens 2, the intraocular lens 2 can be effectively prevented from rotating in its circumferential direction on the setting surface 200b.

Next, the insertion tube 130 of the nozzle body 100 is inserted into the eye from the discission wound of the eye. After the insertion tube 130 is inserted into the eye from the discission wound, the pressing plate member 330 of the plunger 300 is pressed toward the tip 100a of the nozzle body 100. As a result, the tip of the action member 310 of the plunger 300 comes into contact with the circumference part of the optical member 2b of the intraocular lens 2 settled on the setting surface 200a, and then the intraocular lens 2 is guided toward the insertion tube 130 by the plunger 300.

Figure 6:
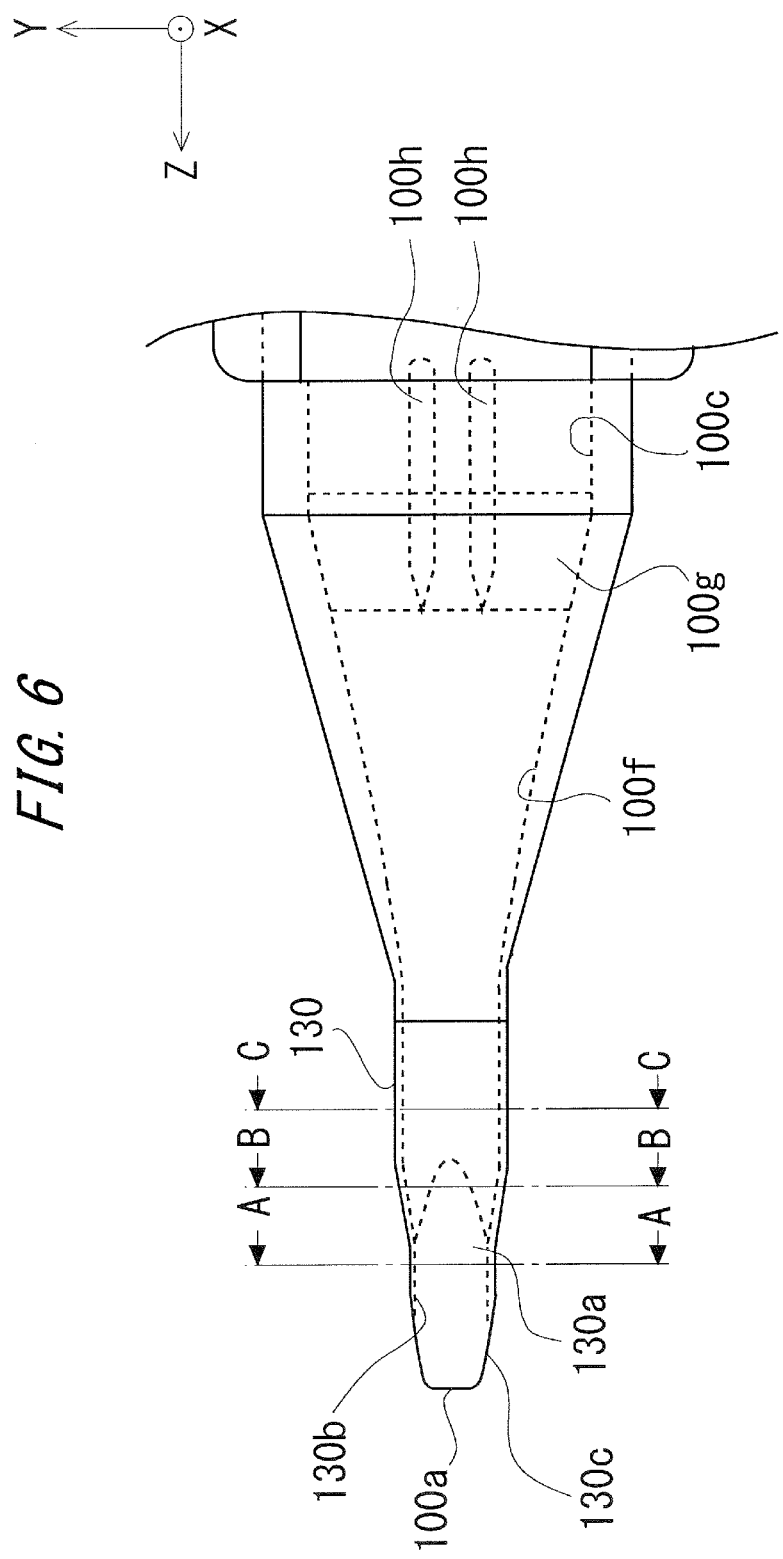
FIG. 6 is a plan detail diagram illustrating a tip of an intraocular lens insertion apparatus according to an embodiment.

Next, the details of the configuration of the part around the tip of the nozzle body 100 are described below. FIG. 6 is a plane diagram illustrating the details of the part around the insertion tube 130 of the nozzle body 100. The contour of the nozzle body 100 is tapering from the stage member 200 toward the tip of the nozzle body 100. A diameter-reducing part 100f is provided for the through-hole 100c. The diameter-reducing part 100f is configured to achieve that the dimension of the bottom surface and the upper surface becomes smaller as the position on the diameter-reducing part 100f becomes closer to the tip 100a. Therefore, the cross-section of the diameter-reducing part 100f becomes also smaller along with the dimension of the bottom surface and the upper surface. And the thickness of the wall of the diameter-reducing part 100f is set to achieve that the diameter-reducing part 100f is not folded when the insertion apparatus 1 is used. It is noted that the bottom surface at the back end of the diameter-reducing part 100f is formed as an oblique surface 100g which rises up toward the positive side of the X axis as the position on the diameter-reducing part 100f becomes closer to the tip 100a. The oblique surface 100g functions an uneven surface.

A pair of introduction protrusions 100h which extends in the Z axis direction of the nozzle body 100 at the bottom surface of the through-hole 100c is formed near the diameter-reducing part 100f. Each introduction protrusion 100h faces each other across the center of the bottom surface of the through-hole 100c. The introduction protrusion 100h runs from before backward on the oblique surface 100. And the introduction protrusions 100h are formed to protrude upward slightly from the bottom surface of the diameter-reducing part 100f and extend in parallel to each other. The height of the introduction protrusion 100h is the same as the height of the oblique surface 100g since the oblique surface 100g rises up as the position on the diameter-reducing part 100f becomes closer to the tip 100a. In addition, the distance between the introduction protrusions 100h is slightly larger than the width of the action member 310 of the plunger 300.

Figure 7:
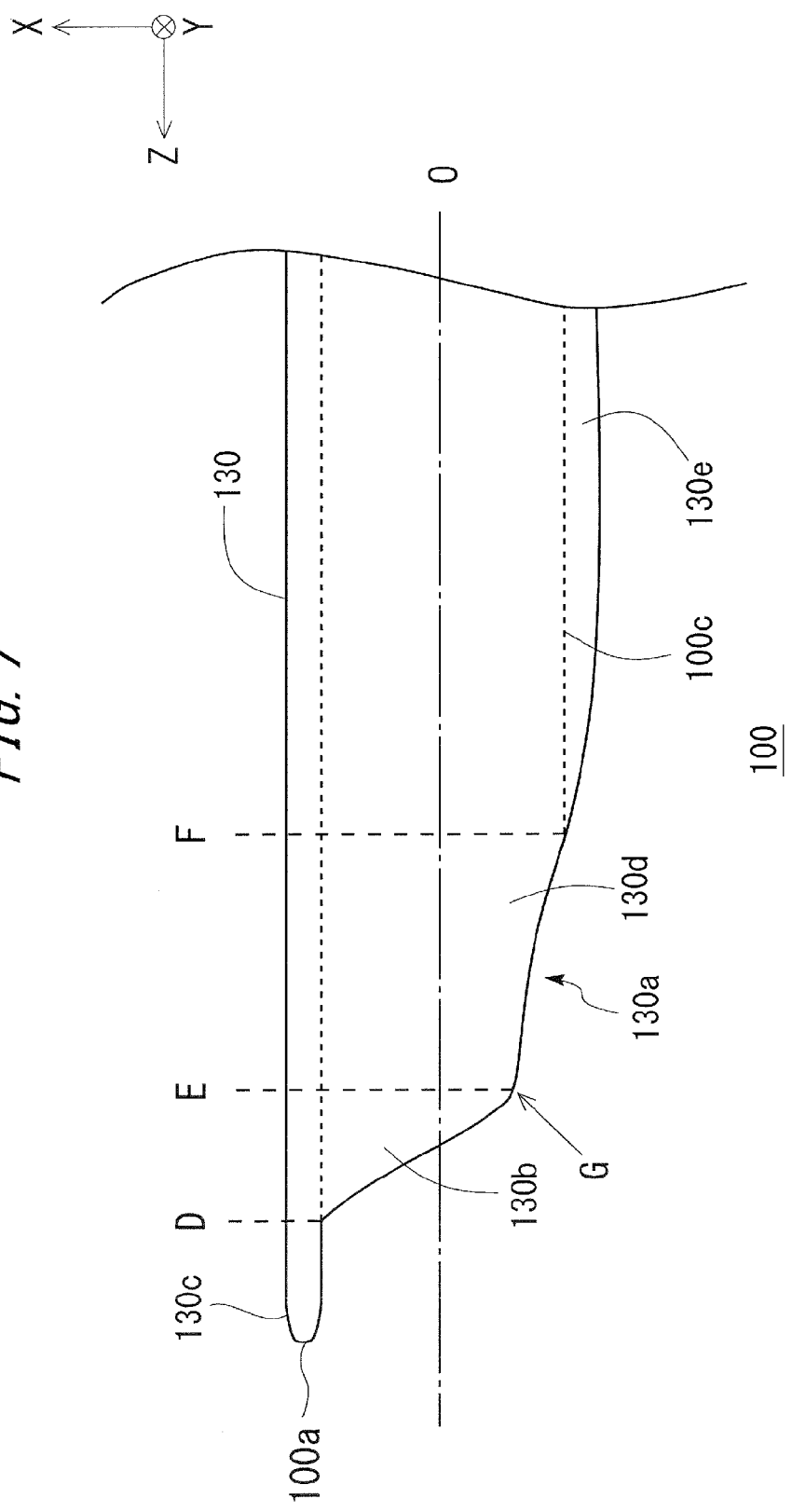
FIG. 7 is a side detail diagram illustrating a tip of an intraocular lens insertion apparatus according to an embodiment.

Further, in the present embodiment, the through-hole 100c is formed to extend in a linear arrangement with the almost the same cross section in the insertion tube 130 as illustrated in FIG. 7. In addition, the through-hole 100c functions as a fore-end opening 130a of the insertion tube 130. Moreover, a fore-end area 130b is provided for the fore-end side of the fore-end opening 130a. And a planate protrusion 130c is provided for the fore-end area 130b. The planate protrusion 130c is formed to extend the direction toward which the plunger 300 is pushed in the nozzle body 100, that is the direction of the movement of the intraocular lens 2 (Z axis direction in FIG. 7).

As illustrated in FIG. 7, the fore-end opening 130a is formed by a plane which descends toward the negative side of the Z axis as the position on the insertion tube 130 moves toward the negative side of the X axis. Namely, the upper side of the insertion tube 130 is formed to be longer in the Z axis direction than the lower side of the insertion tube 130. In addition, the fore-end opening 130a is configured to have an inflection point G at which the curvature of the contour of the fore-end opening 130a changes more dynamically than the curvatures at the other points of the fore-end opening 130a. It is noted here that the side of the fore-end opening 130a closer to the tip 100a than the inflection point G is referred to as the fore-end area 130b of the fore-end opening 130a and the side of the fore-end opening 130a closer to the back-end 100b than the inflection point G is referred to as the back-end area 130d of the fore-end opening 130a.

Further, as illustrated in FIG. 7, the central axis O is defined in the direction which is parallel to the Z axis of the nozzle body 100. The fore-end opening 130a includes the fore-end area 130b and the back-end area 130d. The end surface of the fore-end opening 130a is the oblique surface oblique to the plane which is perpendicular to the central axis O. The angle of gradient of the oblique surface in the fore-end area 130b to the plane which is perpendicular to the central axis O is smaller than the angle of gradient of the oblique surface in the back-end area 130d to the plane which is perpendicular to the central axis O. Therefore, the side wall in the fore-end area 130b rises in the X axis direction in the lateral diagram of the fore-end opening 130a. In addition, the back-end area 130d is connected with the body member 130e while the height of the side wall in the fore-end area 130b progressively increases in the X axis direction. The side wall in the fore-end area 130b extends in the direction of the optical axis, that is the X axis direction in FIG. 7, of the intraocular lens 2 settled on the stage member 210. In addition, the direction which the side wall in the fore-end area 130b extends, that is the X axis direction in FIG. 7 is perpendicular to the direction toward which the plunger 300 is pushed in the nozzle body 100, the direction toward which the intraocular lens 2 moves in the nozzle body 100 and the direction toward which the protrusion 130c extends.

Further, as illustrated in FIG. 6, the contour of the fore-end opening 130a is a shape which is tapering toward the tip 100a. It is noted that although the contour of the fore-end opening 130a in the fore-end area 130b is not a taper in the present embodiment, the contour of the fore-end opening 130a can be configured to be a which is tapering from the back-end area 130d to the fore-end area 130b. With configuration in which the contour of the fore-end opening 130a is tapering, the fore-end opening can be more easily inserted into the discission wound the width of which is smaller than conventional discission wounds.

Figure 8:
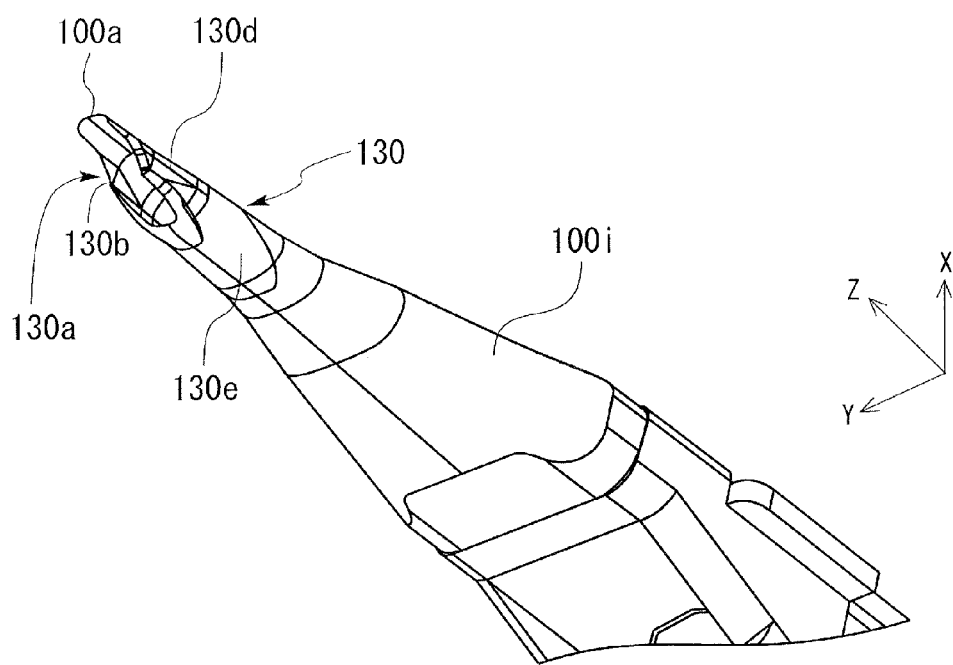
FIG. 8 is a perspective diagram illustrating a tip of an intraocular lens insertion apparatus according to an embodiment.

In addition, as illustrated in FIG. 8, the contour of the nozzle body 100 includes a tapering part 100i which is tapering toward the tip 100a of the nozzle body 100. Further, as illustrated in FIG. 8, the fore-end opening 130a of the insertion tube 130 of the nozzle body 100 includes an opening which opens toward the negative side of the X axis. As illustrated in FIGS. 7 and 8, the insertion tube 130 includes the body member 130e, the back-end area 130d, the fore-end area 130b and the protrusion 130c in this order from the back end 100b to the tip 100a of the nozzle body 100. Additionally, when the insertion tube 130 is divided into portions by planes perpendicular to the Z axis as illustrated in FIG. 7, the part from the plane F to the back end 100b is referred to as the body member 130e, the part from the plane E to the plane F is referred to as the back-end area 130d, the part from the plane D to the plane E is referred to as the fore-end area 130b and the part from the plane D to the tip 100a is referred to as the protrusion 130c.

The body member 130e is a tube member. As illustrated in FIG. 7, the thickness on the bottom side of the body member 130e progressively decreases as the position on the body member 130e is closer to the tip 100a. The body member 130e and the back-end area 130d are smoothly connected with each other at the position indicated by the plane F. The cross-section of the back-end area 130d with respect to the XY plane is configured to be smaller and the contour is a taper. In addition, as illustrated in FIGS. 7 and 8, the height of the side wall in the back-end area 130d in the X axis direction progressively decreases. Therefore, the back-end area 130d is smoothly connected with the body member 130e and the fore-end area 130b.

The fore-end area 130b is configured to have an upper surface which is almost parallel to the YZ plane and a lateral wall which is perpendicular to the upper surface and is almost parallel to the XZ plane. The upper surface in the fore-end area 130b is connected with the protrusion 130c on the side of the tip 100a. FIG. 7 illustrates that the height of the lateral wall in the fore-end area 130b in the X axis direction rapidly increases from the plane D to the plane E. Since the lateral wall in the fore-end area 130b is configured to be elevated just after the protrusion 130c, the intraocular lens 2 can be stably retained and guided into the human crystalline capsule. Further, as illustrated in FIGS. 7 and 8, the protrusion 130c is a planate member which is almost parallel to the YZ plane. The protrusion 130c is configured by extending the upper surface of the fore-end area 130b toward the tip 100a.

Figure 9A:
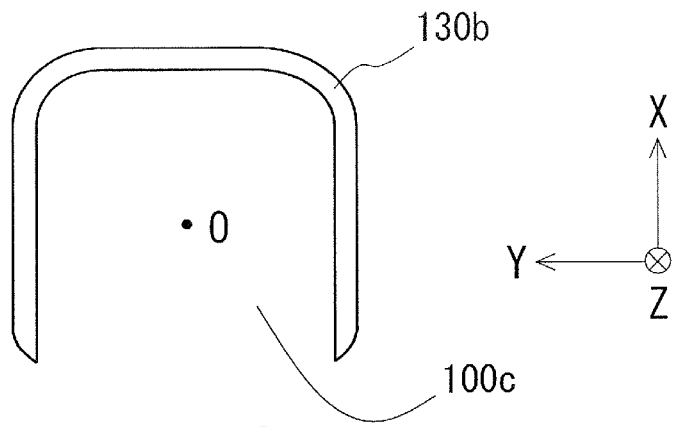
FIGS. 9A to 9C are cross-section diagrams illustrating a insertion tube of an intraocular lens insertion apparatus according to an embodiment.
Figure 9B:
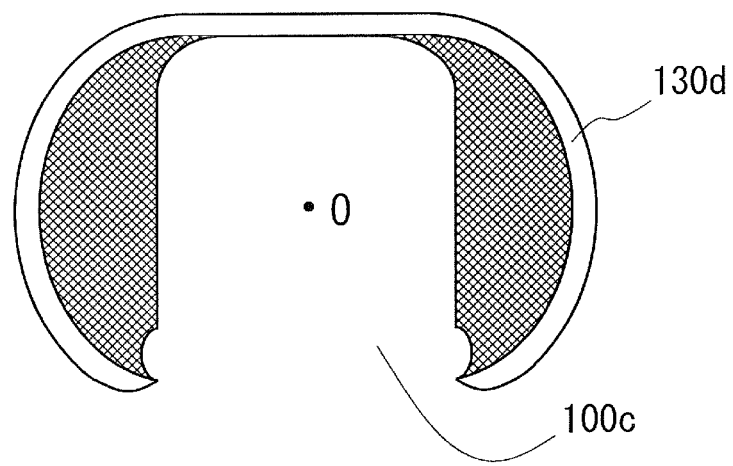
Figure 9C:
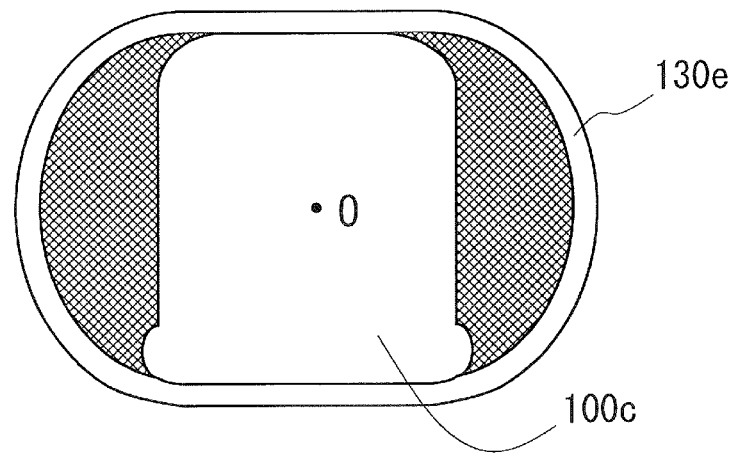

FIG. 9 illustrates three cross-sections of the insertion tube 130 of the nozzle body 100. Specifically, FIG. 9A is a sectional diagram taken along A-A of FIG. 6, FIG. 9B is a sectional diagram taken along B-B of FIG. 6 and FIG. 9C is a sectional diagram taken along C-C of FIG. 6. In addition, FIGS. 9A to 9C illustrate cross-sections of the insertion tube 130 when the insertion tube 130 is viewed from the negative side of the Z axis to the positive side of the Z axis, that is from the back end 100b of the nozzle body 100 to the tip 100a of the nozzle body 100.

As illustrated in FIG. 9A, the fore-end area 130b of the fore-end opening 130a in the cross section thereof is configured by providing a pair of lateral walls which are parallel to the XZ plane and an upper surface which are parallel to the YZ plane and connecting the pair of lateral walls and the upper surface with each other smoothly. In addition, as illustrated in FIG. 9B, the back-end area 130d of the fore-end opening 130a in the cross section thereof is configured by changing the planate lateral wall of the fore-end area 130b into a curved lateral wall. Further, as illustrated in FIG. 9C, the body member 130e in the cross section thereof is configured by providing the upper surface and the lateral wall in the back-end area 130d and a lower surface which faces the upper surface across the central axis O. Moreover, the upper surface, the lower surface and the pair of lateral walls encloses the through-hole 100c.

With the insertion tube 130 configured as described above, when the plunger 300 is pushed, the intraocular lens 2 moves through the tapering part 100i and the body member 130e of the insertion tube 130 and reach the fore-end opening 130a. The intraocular lens 2 moves through the back-end area 130d to the fore-end area 130b, and further moves to the human crystalline capsule with retained by the lateral walls in the fore-end area 130b. Therefore, the intraocular lens 2 can be prevented from going out from the eye when the intraocular lens 2 is moved to the fore-end opening 130a for guiding the intraocular lens 2 into the human crystalline capsule.

In addition, since the protrusion 130c is provided of the tip of the insertion tube 130, the insertion of the insertion tube 130 through a discission wound smaller than a conventional discission wound into the eye can be more easily achieved. Further, since the fore-end area 130b and the back-end area 130d are provided after the protrusion 130c, the intraocular lens 2 can be stably retained and guided into the human crystalline capsule after the insertion tube 130 is inserted into the eye until the insertion tube 130 reaches a predetermined position. And with the configuration as described above, the intraocular lens 2 can be prevented from going out of the eye without the operator's intention. Therefore, according to the intraocular lens insertion apparatus 1 of the present embodiment, the insertion tube 130 can be more easily inserted into a discission wound than conventional insertion tubes and the intraocular lens 2 can be more stably retained and guided into the human crystalline capsule than conventional insertion tubes.

As an example, the insertion apparatus 1 according to the present embodiment is configured to achieve that the length of the protrusion 130c in the Z axis direction is about 1.0 mm, the width of the protrusion 130c in the Y axis direction is from about 1.1 mm to about 1.6 mm, the length of the fore-end area 130b in the Z axis direction is about 1.0 mm, the length of the back-end area 130d is about 1.5 mm, and the width of the insertion tube 130 in the Y axis direction is from about 1.6 mm to about 2.4 mm. In this example, the insertion apparatus 1 can be more easily inserted into a discission wound than conventional insertion apparatuses and the intraocular lens can be more stably retained and guided into the human crystalline capsule than conventional insertion apparatuses.

Although the present embodiment is described as above, the configurations of the intraocular lens insertion apparatus are not limited to those as described above and various variations may be made to the embodiment described herein within the technical scope of the above embodiment. For example, the fore-end opening 130a is configured to have the inflection point G in the side diagram of the insertion tube 130. In addition to this configuration, another inflection point can be provided for the fore-end area 130b and/or the back-end area 130d. Moreover, the contours of the fore-end area 130b and the back-end area 130d can be configured sorely with curves or with combination of linear lines.

In addition, although the protrusion 130c is a planate member which is almost parallel to the YZ plane in the above descriptions, the protrusion 130c can be a member which is, for example, curved in an arc in the cross section by the XY plane. Similarly, although the lateral walls which forms the fore-end area 130b is a pair of lateral walls which is almost parallel to the XZ plane, the lateral walls can be walls which are, for example, curved in an arc in the cross section by the XY plane. Additionally, although the pair of lateral walls is almost parallel to the XZ plane in the above descriptions, the lateral walls can be configured to achieve that the cross section of the lateral walls by the XY plane becomes a V shape or an inverted V shape as long as the lateral walls can retain the intraocular lens.

A variation of the insertion apparatus according to the above embodiment is described below. An fore-end opening, protrusion, an oblique surface, fore-end area and the like the configurations of which are similar to those in the above embodiment are provided for the insertion apparatus according to the variation. Therefore, when the insertion apparatus according to the variation can also be more easily inserted into a discission wound than conventional insertion apparatuses and the intraocular lens can be more stably retained and guided into the human crystalline capsule than conventional insertion apparatuses.

In addition, the contour of the nozzle body of the insertion apparatus according to the variation is modified within the technical scope of the above embodiment. As an example, a needle hole 1200 into which a tip of a needle of a syringe filled with viscoelastic material is inserted and a guide wall 1110 for guiding the tip of the needle of the syringe to the needle hole 1200 are provided for the stage lid member 1120 of the nozzle body 1100 as illustrated in FIG. 10. In addition, a three-piece intraocular lens 1002 is set instead of the one-piece intraocular lens 2 of the above embodiment. However, since the fore-end side of the nozzle body 1100 is configured similar to the fore-end side of the nozzle body 100 as described above, the modifications of the configurations of the insertion apparatus in the present variation still achieve the effect achieved by the insertion apparatus according to the above embodiment.

Figure 10A:
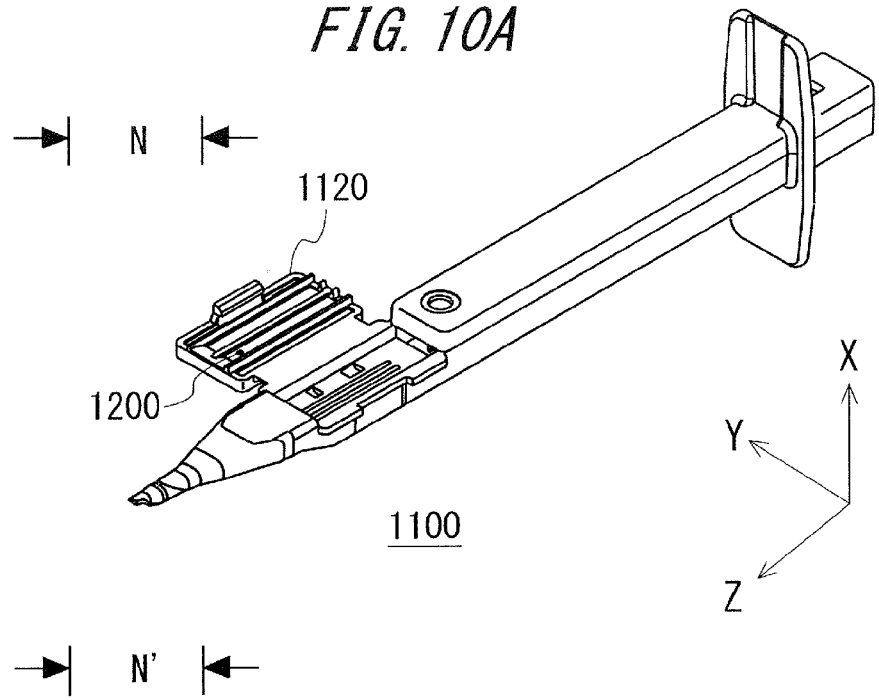
FIG. 10A is a perspective diagram illustrating a nozzle body of an intraocular lens insertion apparatus according to a variation example.
Figure 10B:
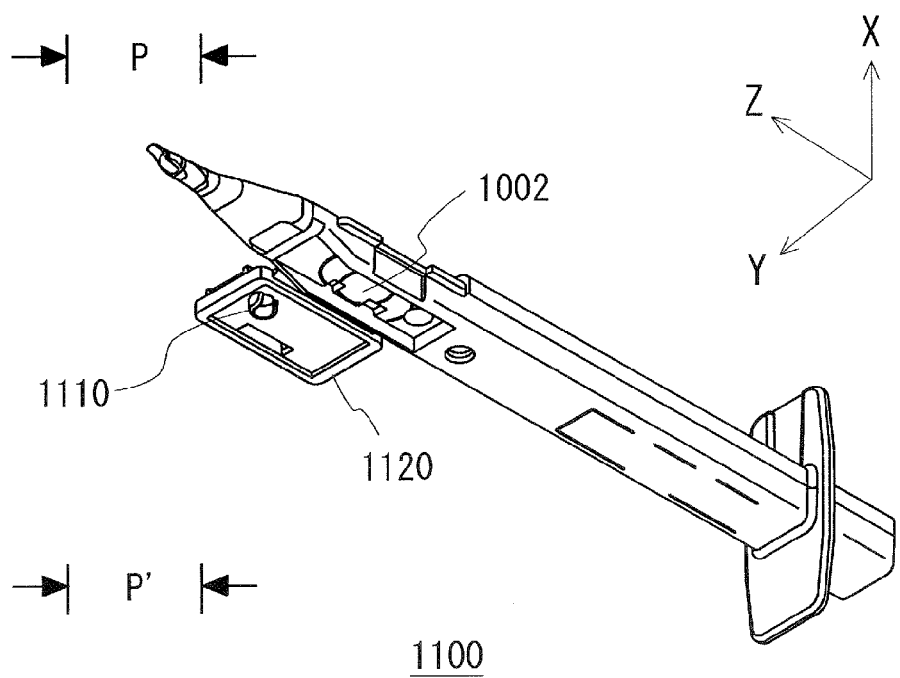
FIG. 10B is a perspective diagram illustrating a nozzle body of an intraocular lens insertion apparatus according to a variation example.
Figure 10C:
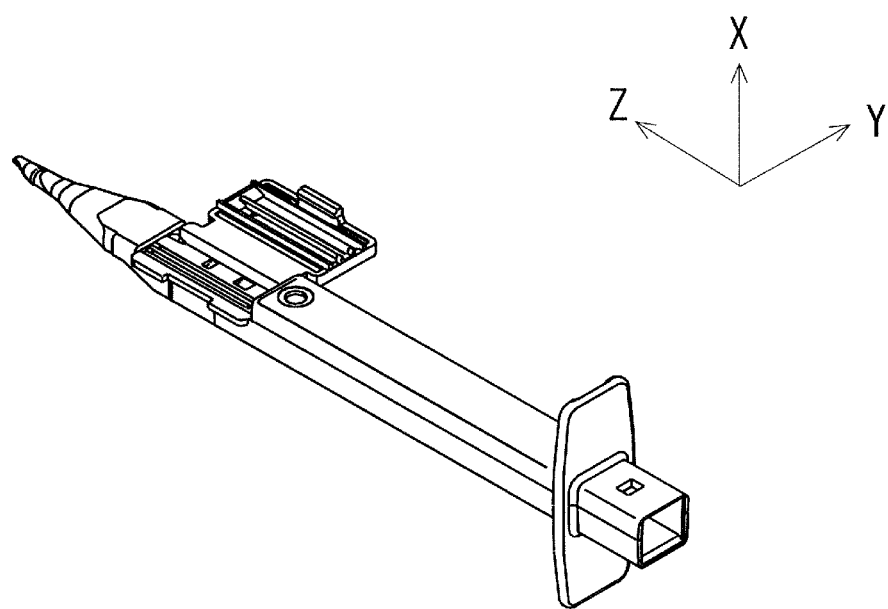
FIG. 10C is a perspective diagram illustrating a nozzle body of an intraocular lens insertion apparatus according to a variation example.
Figure 10D:
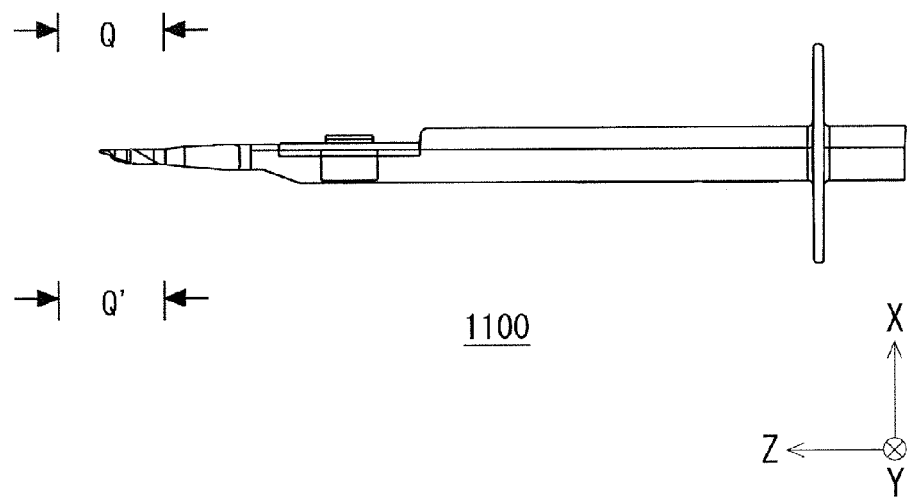
FIG. 10D is a diagram illustrating a nozzle body of an intraocular lens insertion apparatus according to a variation example.
Figure 10E:
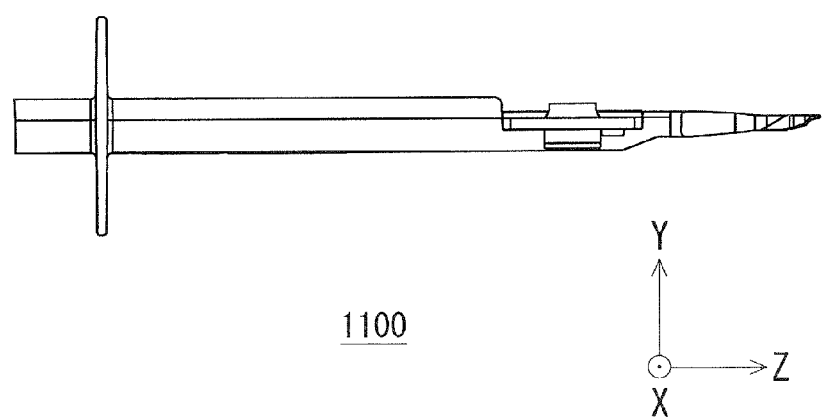
FIG. 10E is a diagram illustrating a nozzle body of an intraocular lens insertion apparatus according to a variation example.
Figure 10F:
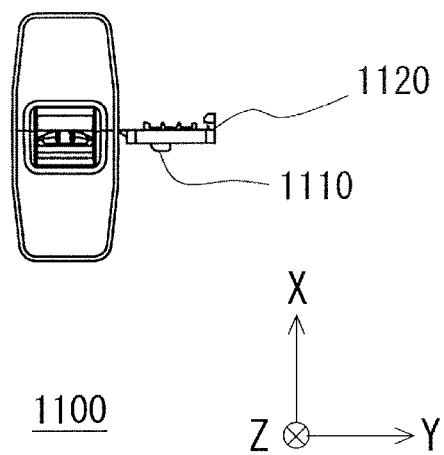
FIG. 10F is a diagram illustrating a nozzle body of an intraocular lens insertion apparatus according to a variation example.
Figure 10G:
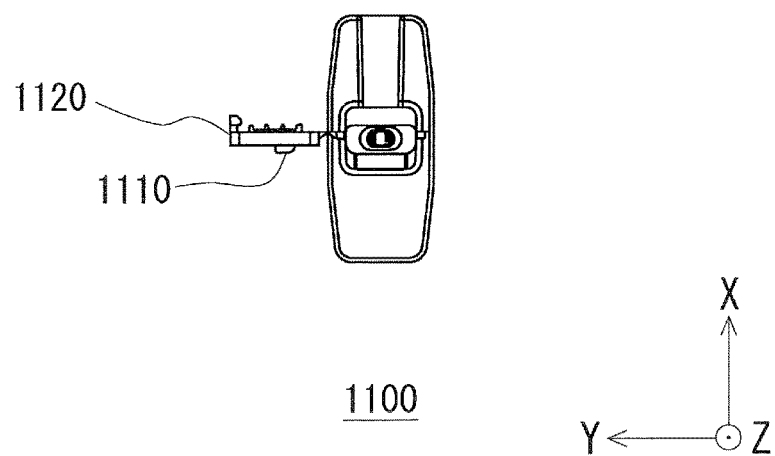
FIG. 10G is a diagram illustrating a nozzle body of an intraocular lens insertion apparatus according to a variation example.
Figure 10H:
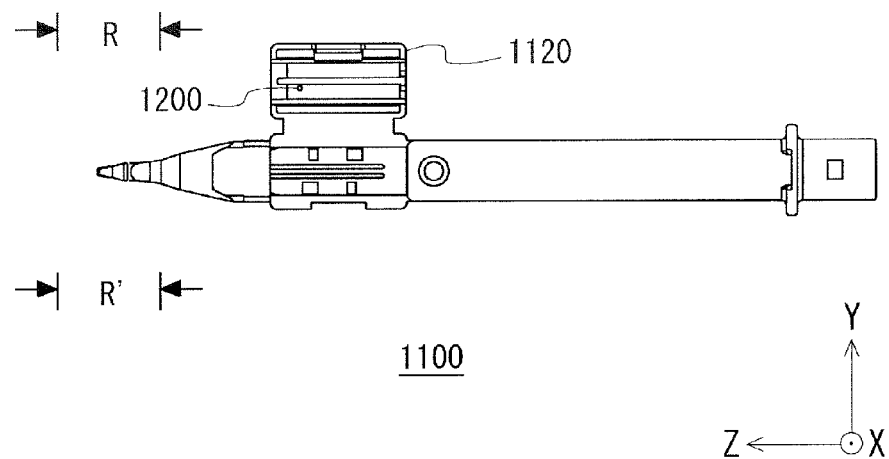
FIG. 10H is a diagram illustrating a nozzle body of an intraocular lens insertion apparatus according to a variation example.
Figure 10I:
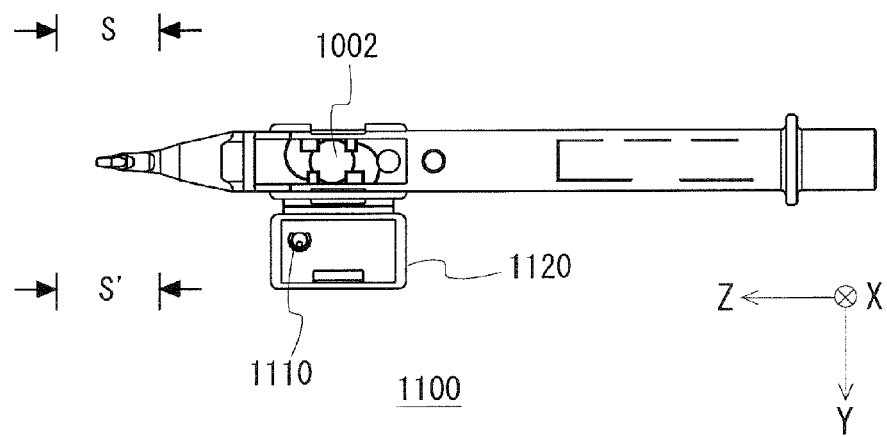
FIG. 10I is a diagram illustrating a nozzle body of an intraocular lens insertion apparatus according to a variation example.

FIGS. 10A to 10C are perspective diagrams illustrating the nozzle body 1100 of the insertion apparatus according to the variation. FIG. 10D is a diagram of the nozzle body 1100 when the nozzle body 1100 is viewed in the direction from the negative side of the Y axis to the positive side of the Y axis. FIG. 10E is a diagram of the nozzle body 1100 when the nozzle body 1100 is viewed in the direction from the positive side of the X axis to the negative side of the X axis. FIG. 10F is a diagram of the nozzle body 1100 when the nozzle body 1100 is viewed in the direction from the negative side of the Z axis to the positive side of the Z axis. FIG. 10G is a diagram of the nozzle body 1100 when the nozzle body 1100 is viewed in the direction from the positive side of the Z axis to the negative side of the Z axis. FIG. 10H is a diagram of the nozzle body 1100 when the nozzle body 1100 is viewed in the direction from the positive side of the X axis to the negative side of the X axis. FIG. 10I is a diagram of the nozzle body 1100 when the nozzle body 1100 is viewed in the direction from the negative side of the X axis to the positive side of the X axis.

Figure 10J:
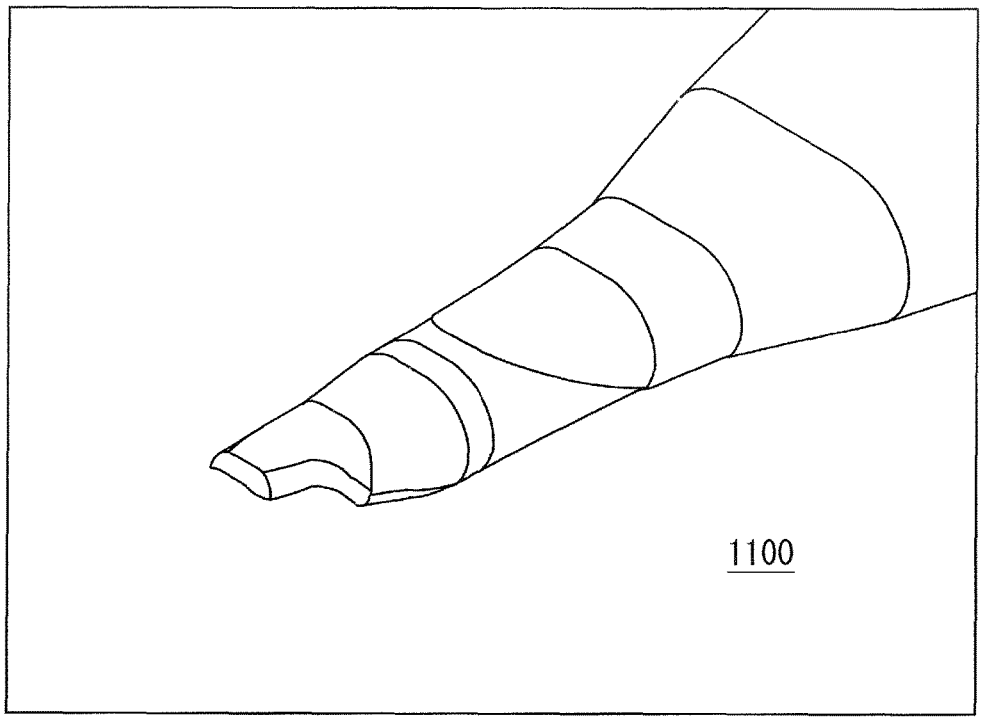
FIG. 10J is a partial enlarged diagram illustrating a nozzle body of an intraocular lens insertion apparatus according to a variation example.
Figure 10K:
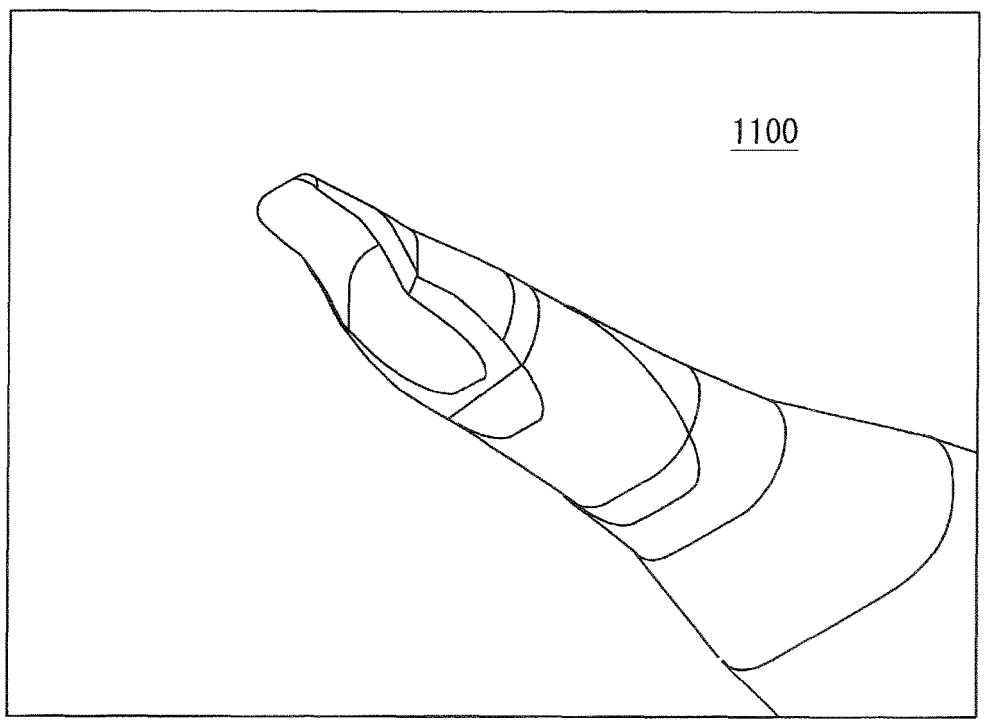
FIG. 10K is a partial enlarged diagram illustrating a nozzle body of an intraocular lens insertion apparatus according to a variation example.
Figure 10L:
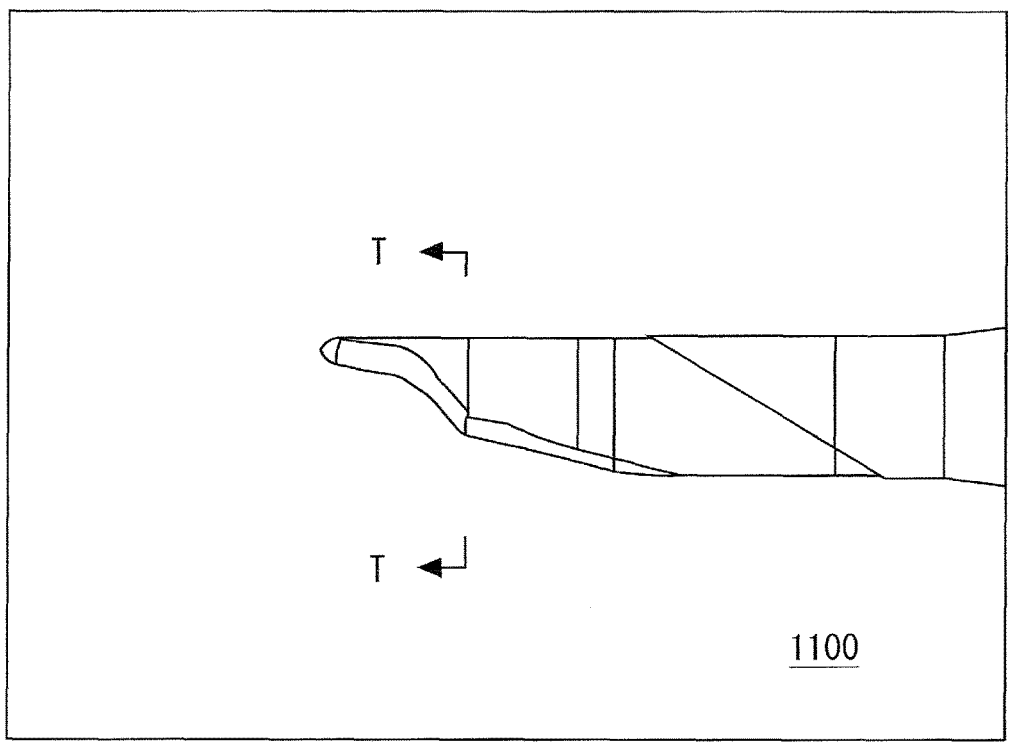
FIG. 10L is a partial enlarged diagram illustrating a nozzle body of an intraocular lens insertion apparatus according to a variation example.
Figure 10M:
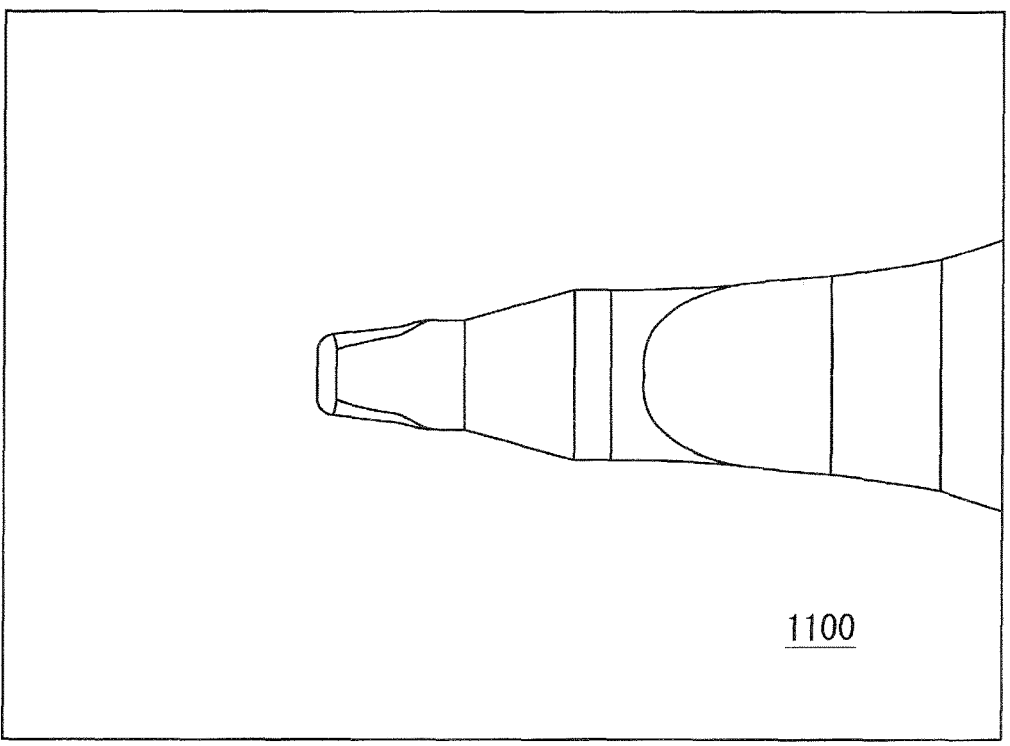
FIG. 10M is a partial enlarged diagram illustrating a nozzle body of an intraocular lens insertion apparatus according to a variation example.
Figure 10N:
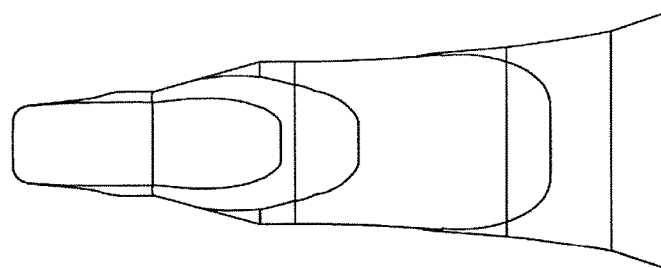
FIG. 10N is a partial enlarged diagram illustrating a nozzle body of an intraocular lens insertion apparatus according to a variation example.
Figure 10P:
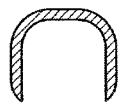
FIG. 10P is a cross-section diagram illustrating a nozzle body of an intraocular lens insertion apparatus according to a variation example.

FIG. 10J is a partial enlarged diagram illustrating the area of the nozzle body 1100 indicated by "N" and "N'" in FIG. 10A. FIG. 10K is a partial enlarged diagram illustrating the area of the nozzle body 1100 indicated by "P" and "P'" in FIG. 10B. FIG. 10L is a partial enlarged diagram illustrating the area of the nozzle body 1100 indicated by "Q" and "Q'" in FIG. 10D. FIG. 10M is a partial enlarged diagram illustrating the area of the nozzle body 1100 indicated by "R" and "R'" in FIG. 10H. FIG. 10N is a partial enlarged diagram illustrating the area of the nozzle body 1100 indicated by "S" and "S'" in FIG. 10I. FIG. 10P is a cross-section diagram of the nozzle body 1100 taken along T-T of FIG. 10L.

Figure 11A:
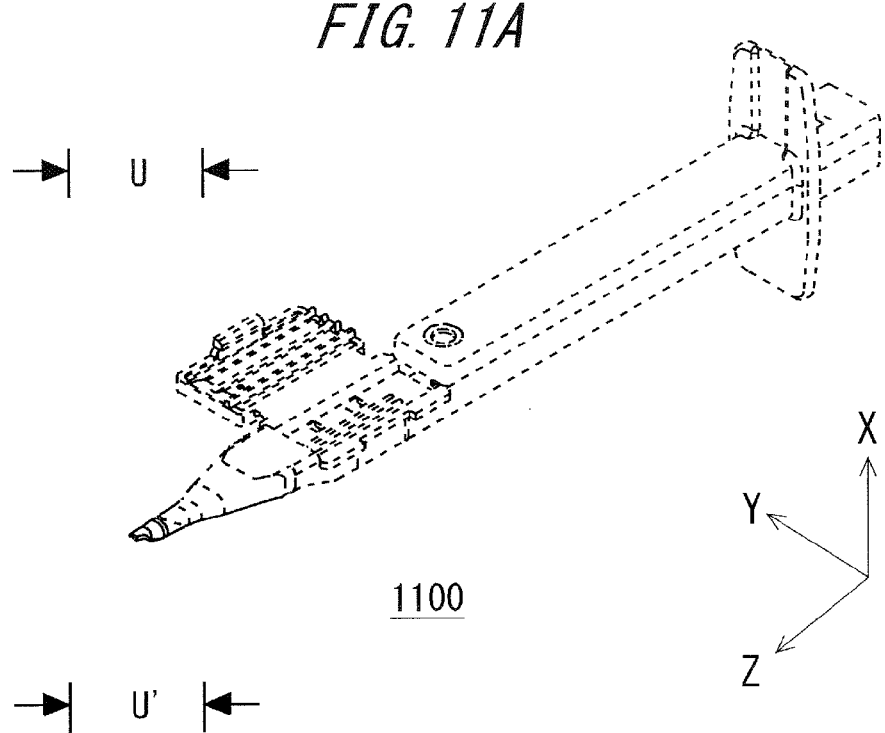
FIG. 11A is a perspective diagram illustrating a nozzle body of an intraocular lens insertion apparatus according to a variation example.
Figure 11B:
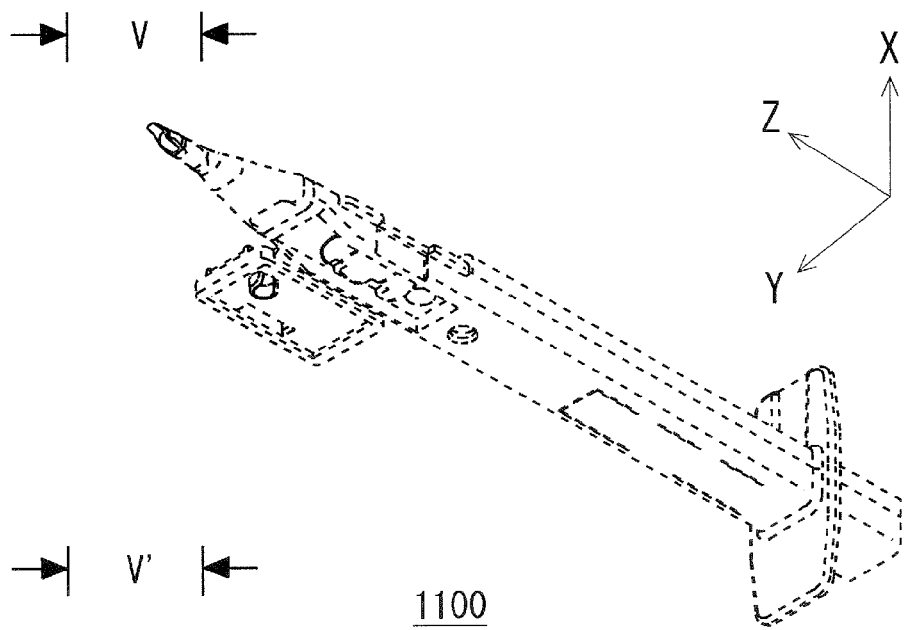
FIG. 11B is a perspective diagram illustrating a nozzle body of an intraocular lens insertion apparatus according to a variation example.
Figure 11C:
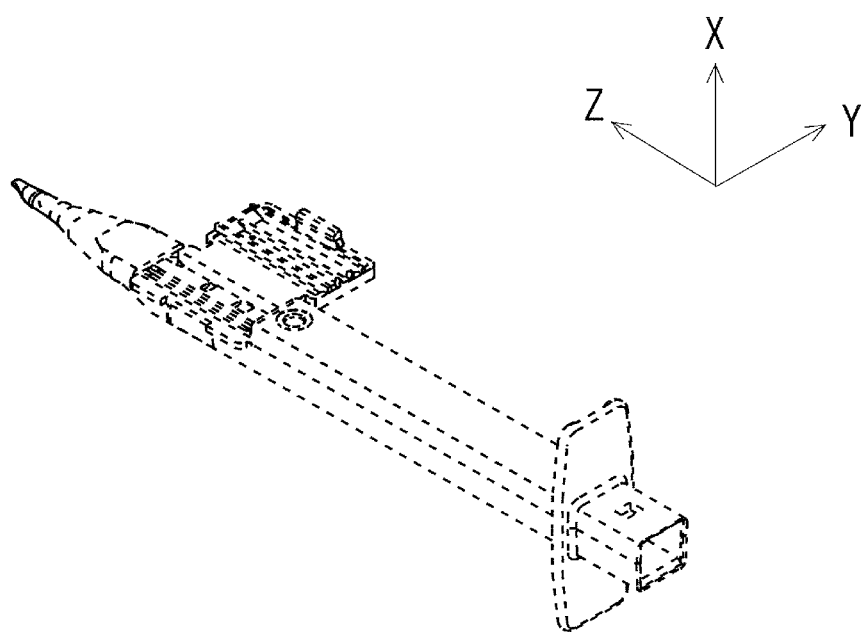
FIG. 11C is a perspective diagram illustrating a nozzle body of an intraocular lens insertion apparatus according to a variation example.
Figure 11D:
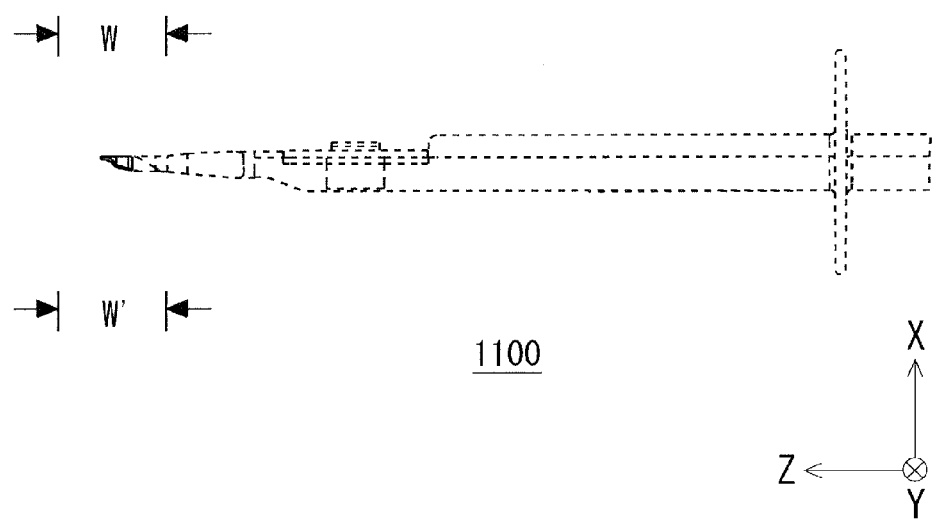
FIG. 11D is a diagram illustrating a nozzle body of an intraocular lens insertion apparatus according to a variation example.
Figure 11E:
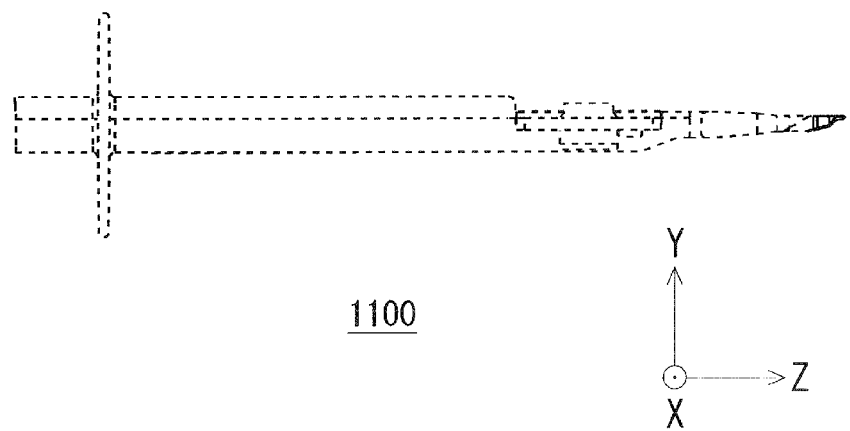
FIG. 11E is a diagram illustrating a nozzle body of an intraocular lens insertion apparatus according to a variation example.
Figure 11F:
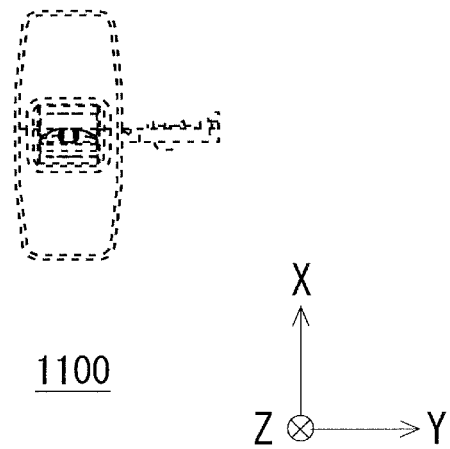
FIG. 11F is a diagram illustrating a nozzle body of an intraocular lens insertion apparatus according to a variation example.
Figure 11G:
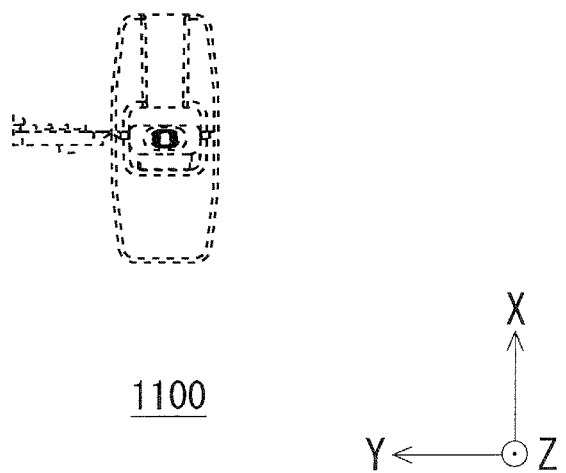
FIG. 11G is a diagram illustrating a nozzle body of an intraocular lens insertion apparatus according to a variation example.

And FIGS. 11A to 11C are perspective diagrams illustrating the nozzle body of the insertion apparatus according to the variation. FIG. 11D is a diagram of the nozzle body 1100 when the nozzle body 1100 is viewed in the direction from the negative side of the Y axis to the positive side of the Y axis. FIG. 11E is a diagram of the nozzle body 1100 when the nozzle body 1100 is viewed in the direction from the positive side of the X axis to the negative side of the X axis. FIG. 11G is a diagram of the nozzle body 1100 when the nozzle body 1100 is viewed in the direction from the positive side of the Z axis to the negative side of the Z axis. FIG. 11H is a diagram of the nozzle body 1100 when the nozzle body 1100 is viewed in the direction from the positive side of the X axis to the negative side of the X axis. FIG. 11I is a diagram of the nozzle body 1100 when the nozzle body 1100 is viewed in the direction from the negative side of the X axis to the positive side of the X axis.

Figure 11J:
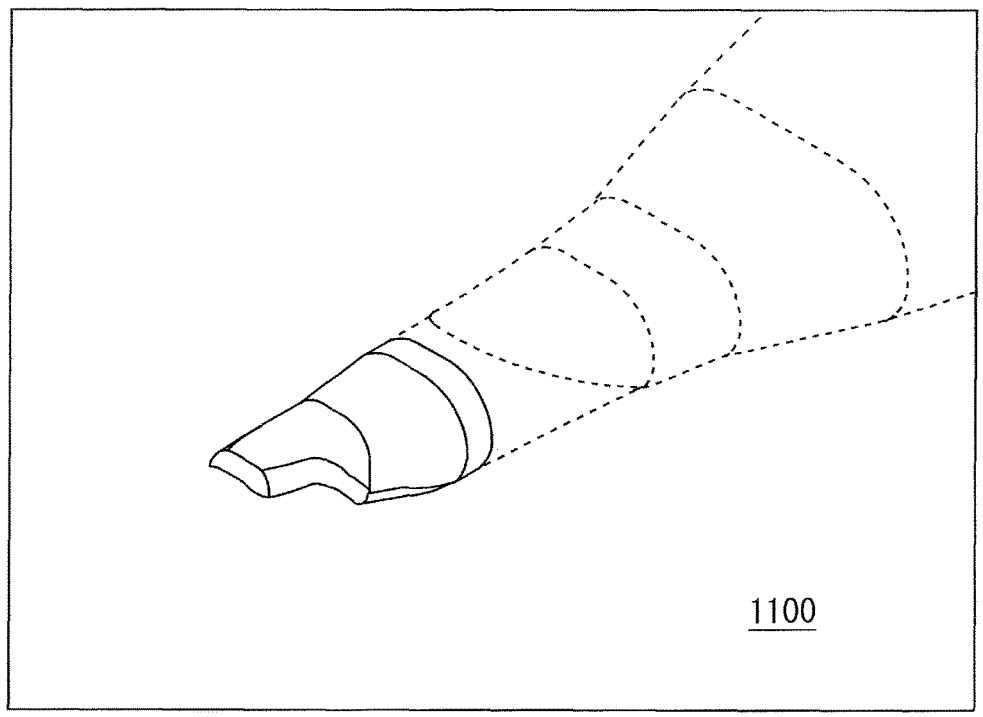
FIG. 11J is a partial enlarged diagram illustrating a nozzle body of an intraocular lens insertion apparatus according to a variation example.
Figure 11K:
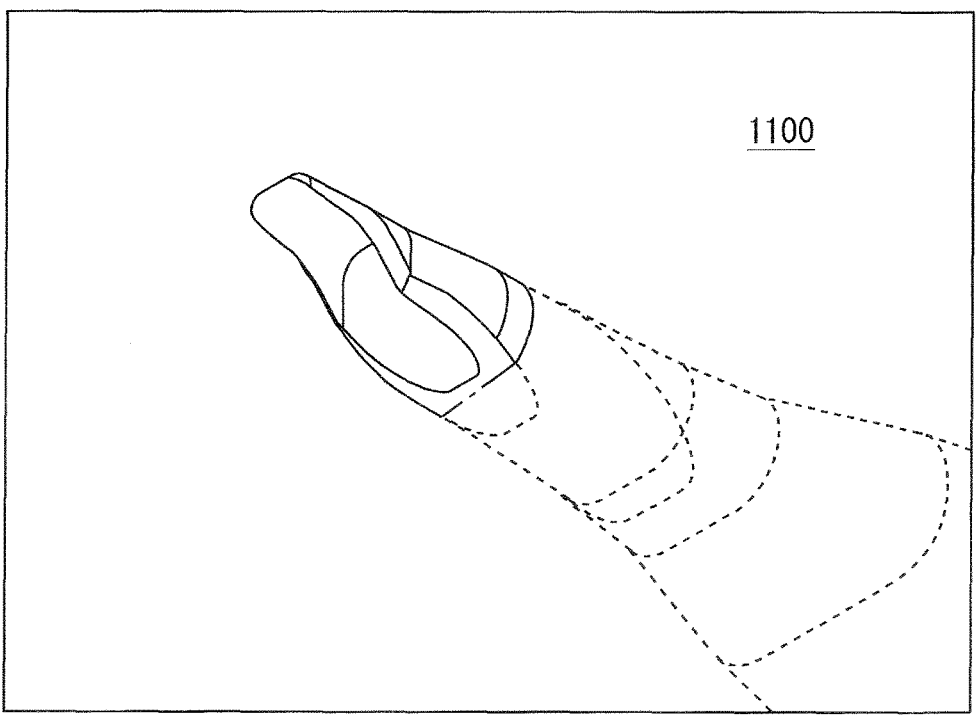
FIG. 11K is a partial enlarged diagram illustrating a nozzle body of an intraocular lens insertion apparatus according to a variation example.
Figure 11L:
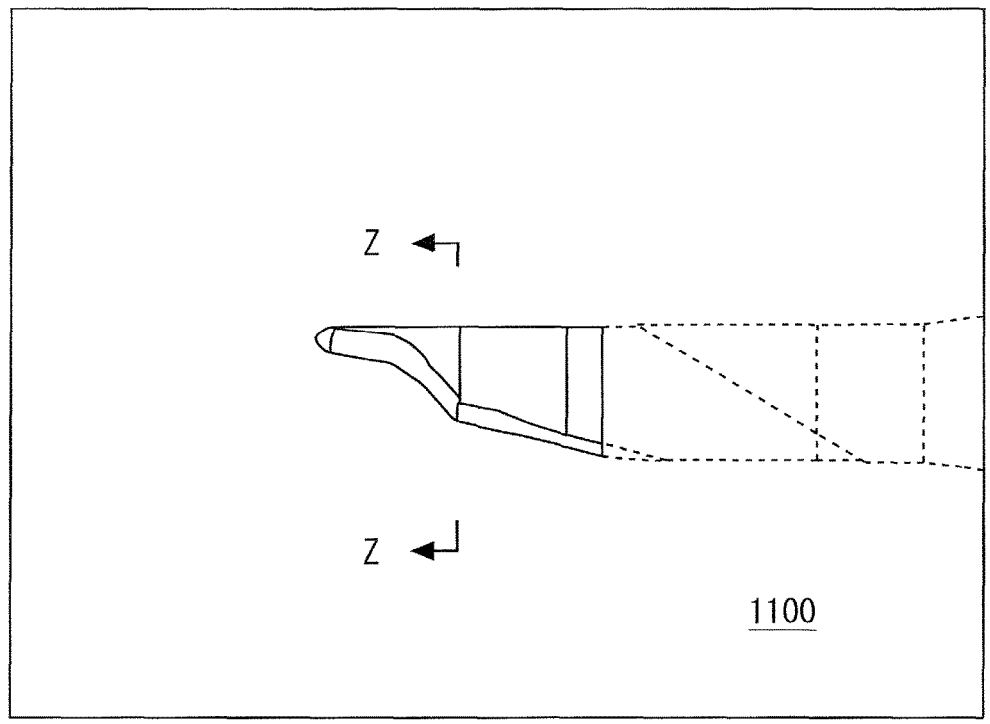
FIG. 11L is a partial enlarged diagram illustrating a nozzle body of an intraocular lens insertion apparatus according to a variation example.
Figure 11M:
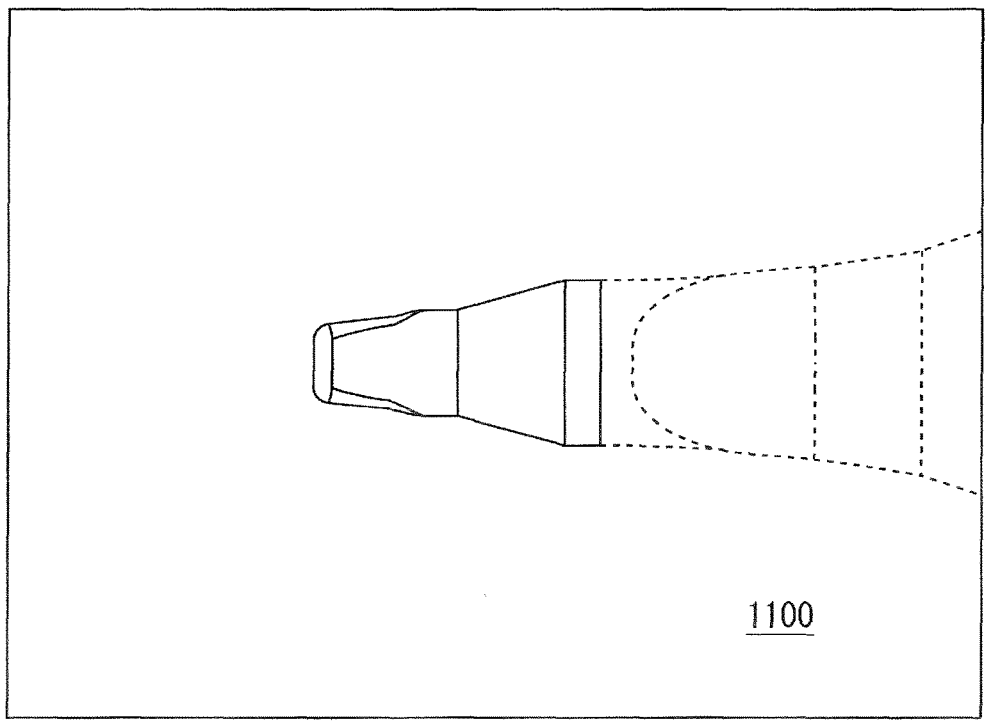
FIG. 11M is a partial enlarged diagram illustrating a nozzle body of an intraocular lens insertion apparatus according to a variation example.
Figure 11N:
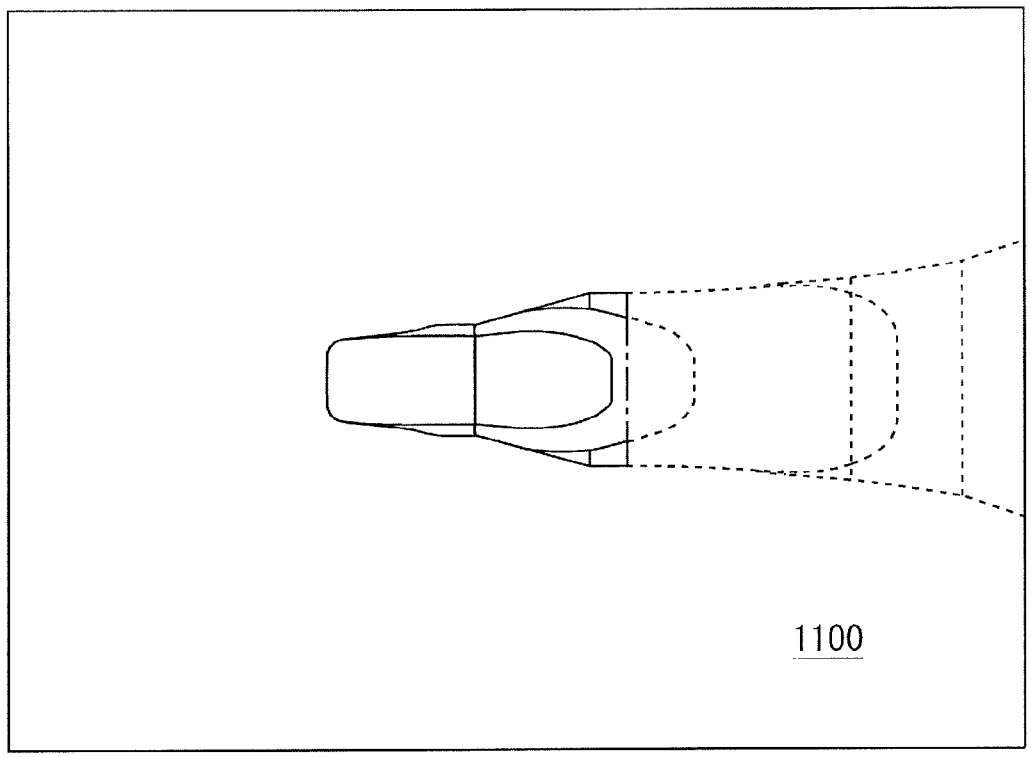
FIG. 11N is a partial enlarged diagram illustrating a nozzle body of an intraocular lens insertion apparatus according to a variation example.
Figure 11P:
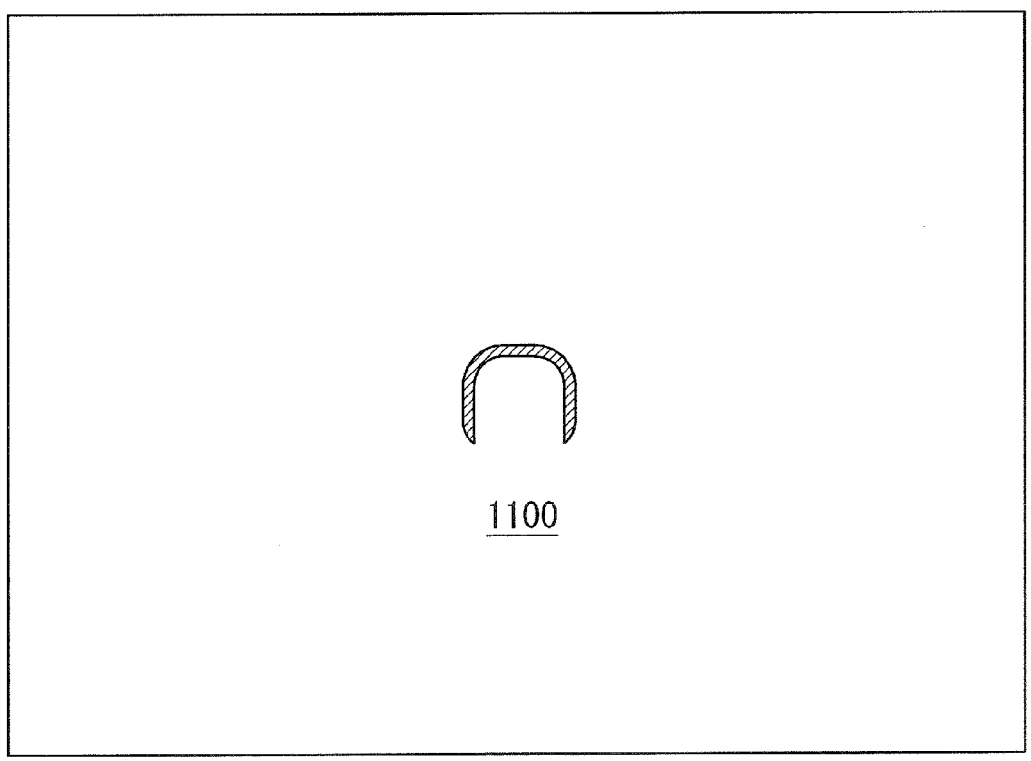
FIG. 11P is a cross-section diagram illustrating a nozzle body of an intraocular lens insertion apparatus according to a variation example.

FIG. 11J is a partial enlarged diagram illustrating the area of the nozzle body 1100 indicated by "U" and "U'" in FIG. 11A. FIG. 11K is a partial enlarged diagram illustrating the area of the nozzle body 1100 indicated by "V" and "V'" in FIG. 11B. FIG. 11L is a partial enlarged diagram illustrating the area of the nozzle body 1100 indicated by "W" and "W'" in FIG. 11D. FIG. 11M is a partial enlarged diagram illustrating the area of the nozzle body 1100 indicated by "X" and "X'" in FIG. 11H. FIG. 11N is a partial enlarged diagram illustrating the area of the nozzle body 1100 indicated by "Y" and "Y'" in FIG. 11I. FIG. 11P is a cross-section diagram of the nozzle body 1100 taken along Z-Z of FIG. 11L.

REFERENCE SIGNS LIST

1 Insertion Apparatus
2, 1002 Intraocular Lens
100, 1100 Nozzle Body
100a Tip of the Nozzle Body
100b Back End of the Nozzle Body
100c Through Hole
130 Insertion Tube
130a Fore-end Opening
130b Fore-end Area
130c Protrusion
130d Back-end Area
130e Body Member
200 Stage Member
210 Positioning Member
220, 1120 Stage Lid Member
300 Plunger
1110 Guide Wall
1200 Needle Hole

What is claimed is:

1. An intraocular lens insertion apparatus, comprising:
a cylindrical body member configured to retain an intraocular lens;
a fore-end opening comprising a fore-end area provided for a tip of the body member; and
a planate protrusion provided for a tip of the fore-end opening,
wherein an end surface of the fore-end area of the fore-end opening is an oblique surface which is oblique to a plane perpendicular to a central axis of the body member,
wherein the fore-end area comprises a pair of lateral walls which are parallel to each other across the central axis, wherein the pair of lateral walls is formed on a side of the fore-end area, and
wherein the planate protrusion is configured to extend from the fore-end area to a distal end of the intraocular lens insertion apparatus, wherein the planate protrusion does not comprise a lateral wall or a bottom surface, such that the planate protrusion is open on both lateral sides and a bottom side thereof,
wherein the fore-end opening further comprises a back-end area connected to the fore-end area, and the back-end area comprises a pair of lateral walls,
wherein the lateral walls of the fore-end area increases in height from the distal end thereof to the proximal end thereof at a first slope,
wherein the lateral walls of the back-end area increases in height from the distal end thereof to the proximal end thereof at a second slope, and
wherein the first slope is greater than the second slope.

2. The intraocular lens insertion apparatus according to claim 1, wherein a contour of the fore-end opening in a side view includes an inflection point between the fore-end area and the back-end area.

3. The intraocular lens insertion apparatus according to claim 2, wherein a shape of the fore-end opening is tapering toward the tip of the fore-end opening.

4. The intraocular lens insertion apparatus according to claim 3, wherein the body member comprises a positioning member for positioning the intraocular lens, and the intraocular lens is positioned by the positioning member in the body member in advance.

5. The intraocular lens insertion apparatus according to claim 2, wherein the body member comprises a positioning member for positioning the intraocular lens, and the intraocular lens is positioned by the positioning member in the body member in advance.

6. The intraocular lens insertion apparatus according to claim 1, wherein a shape of the fore-end opening is tapering toward the tip of the fore-end opening.

7. The intraocular lens insertion apparatus according to claim 6, wherein the body member comprises a positioning member for positioning the intraocular lens, and the intraocular lens is positioned by the positioning member in the body member in advance.

8. The intraocular lens insertion apparatus according to claim 1, wherein the body member comprises a positioning member for positioning the intraocular lens, and the intraocular lens is positioned by the positioning member in the body member in advance.

* * * * *